(12) United States Patent
Noda et al.

(10) Patent No.: US 11,225,984 B2
(45) Date of Patent: Jan. 18, 2022

(54) ACTUATOR DEVICE, HUMANOID ROBOT AND POWER ASSIST DEVICE

(71) Applicants: ADVANCED TELECOMMUNICATIONS RESEARCH INSTITUTE INTERNATIONAL, Kyoto (JP); OSAKA UNIVERSITY, Suita (JP)

(72) Inventors: Tomoyuki Noda, Soraku-gun (JP); Yoshihiro Nakata, Suita (JP); Hiroshi Ishiguro, Suita (JP); Jun Morimoto, Soraku-gun (JP)

(73) Assignees: ADVANCED TELECOMMUNICATIONS RESEARCH INSTITUTE INTERNATIONAL, Soraku (JP); OSAKA UNIVERSITY, Suita (JP)

( * ) Notice: Subject to any disclaimer, the term of this patent is extended or adjusted under 35 U.S.C. 154(b) by 597 days.

(21) Appl. No.: 15/313,791

(22) PCT Filed: May 27, 2015

(86) PCT No.: PCT/JP2015/065173
§ 371 (c)(1),
(2) Date: Nov. 23, 2016

(87) PCT Pub. No.: WO2015/182634
PCT Pub. Date: Dec. 3, 2015

(65) Prior Publication Data
US 2017/0198728 A1 Jul. 13, 2017

(30) Foreign Application Priority Data

May 27, 2014 (JP) .............................. JP2014-109213
Dec. 26, 2014 (JP) .............................. JP2014-266466

(51) Int. Cl.
*F15B 15/08* (2006.01)
*F15B 15/14* (2006.01)
(Continued)

(52) U.S. Cl.
CPC .............. *F15B 15/088* (2013.01); *A61F 2/70* (2013.01); *A61H 3/00* (2013.01); *B25J 9/0006* (2013.01);
(Continued)

(58) Field of Classification Search
CPC .. H02K 41/031; H02K 41/0352; H02K 33/16; F04B 35/045; F15B 15/088;
(Continued)

(56) References Cited

U.S. PATENT DOCUMENTS 5,166,563 A * 11/1992 Bassine ................. F04B 35/045
                                                    128/205.18
5,440,183 A   8/1995 Denne
(Continued)

FOREIGN PATENT DOCUMENTS

CN   103795168 A   5/2014
JP   64-15509 A    1/1989
(Continued)

OTHER PUBLICATIONS

Hayashi et al., "A Newly Developed High Torque and High Precise Indexing Mechanism with Hybrid-Actuator", The 7th Manufacturing and Machine Tool Conference, 2008, pp. 207-208, with an English abstract.
(Continued)

*Primary Examiner* — Abiy Teka
(74) *Attorney, Agent, or Firm* — Birch, Stewart, Kolasch & Birch, LLP

(57) ABSTRACT

[Object] To provide a compact, high-output actuator device allowing force control.
(Continued)

[Solution] An actuator device 1000 includes an electromagnetic coil member 110 provided over a prescribed width on an outer circumference of a cylinder 100, and a movable element 200 slidable as a piston in the cylinder 100. The movable element 200 has a magnetic member 202, and is moved relatively by excitation of the electromagnetic coil member 110. Fluid is supplied to first and second chambers 106a and 106b such that when the movable element 200 is to be moved relatively, the movable element 200 is driven in the same direction.

5 Claims, 20 Drawing Sheets

(51) Int. Cl.
| | |
|---|---|
| F15B 21/08 | (2006.01) |
| H02K 33/16 | (2006.01) |
| H02K 41/03 | (2006.01) |
| H02K 7/20 | (2006.01) |
| B25J 19/00 | (2006.01) |
| B25J 11/00 | (2006.01) |
| A61F 2/70 | (2006.01) |
| A61H 3/00 | (2006.01) |
| B25J 9/00 | (2006.01) |
| F15B 15/12 | (2006.01) |
| F15B 15/20 | (2006.01) |
| H02K 41/035 | (2006.01) |

(52) U.S. Cl.
CPC .............. *B25J 11/00* (2013.01); *B25J 19/00* (2013.01); *F15B 15/125* (2013.01); *F15B 15/14* (2013.01); *F15B 15/20* (2013.01); *F15B 21/08* (2013.01); *H02K 7/20* (2013.01); *H02K 33/16* (2013.01); *H02K 41/03* (2013.01); *H02K 41/031* (2013.01); *H02K 41/0352* (2013.01); *F15B 2015/206* (2013.01)

(58) Field of Classification Search
CPC .. F15B 2013/0448; F15B 11/16; F15B 21/08; E02F 9/2267
See application file for complete search history.

(56) References Cited

U.S. PATENT DOCUMENTS

| | | |
|---|---|---|
| 6,268,667 B1 | 7/2001 | Denne |
| 6,868,822 B1 | 3/2005 | Di Pietro |
| 2008/0258654 A1 | 10/2008 | Neff |
| 2009/0013862 A1 | 1/2009 | Schlipf et al. |
| 2011/0020156 A1* | 1/2011 | Van Brunt .............. F04B 17/04 417/416 |
| 2011/0052430 A1 | 3/2011 | Dehnen et al. |
| 2014/0103770 A1 | 4/2014 | Brahmavar |

FOREIGN PATENT DOCUMENTS

| | | | | |
|---|---|---|---|---|
| JP | 11-153103 A | | 6/1999 | |
| JP | 2001-136728 A | | 5/2001 | |
| JP | 2002-147209 A | | 5/2002 | |
| JP | 2004-282957 A | | 10/2004 | |
| JP | 2010-517505 A | | 5/2010 | |
| JP | 2010-196777 A | | 9/2010 | |
| JP | 2011-193641 A | | 9/2011 | |
| JP | 2011193641 A | * | 9/2011 | ........... H02K 41/031 |
| JP | 2011-214624 A | | 10/2011 | |
| JP | 2012-45194 A | | 3/2012 | |
| WO | WO 2007/139135 A1 | | 12/2007 | |

OTHER PUBLICATIONS

Higo et al., "Dynamic Characteristic and Power Consumption on an Electro-Pneumatic Hybrid Positioning System", Proceedings of the 6th JFPS International Symposium on Fluid Power, Nov. 7-10, 2005, pp. 363-368.

Mills, "Hybrid Actuator for Robot Manipulators: Design, Control and Performance", Proc. of ICRA,1990, pp. 1872-1878.

Sardellitti et al., "Air Muscle Controller Design in the Distributed Macro-Mini (DM$^2$) Actuation Approach," Proceedings of the 2007 IEEE/RSJ International Conference on Intelligent Robots and Systems, San Diego, CA, USA, WeB 2.1, Oct. 29-Nov. 2, 2007, pp. 1822-1827.

* cited by examiner

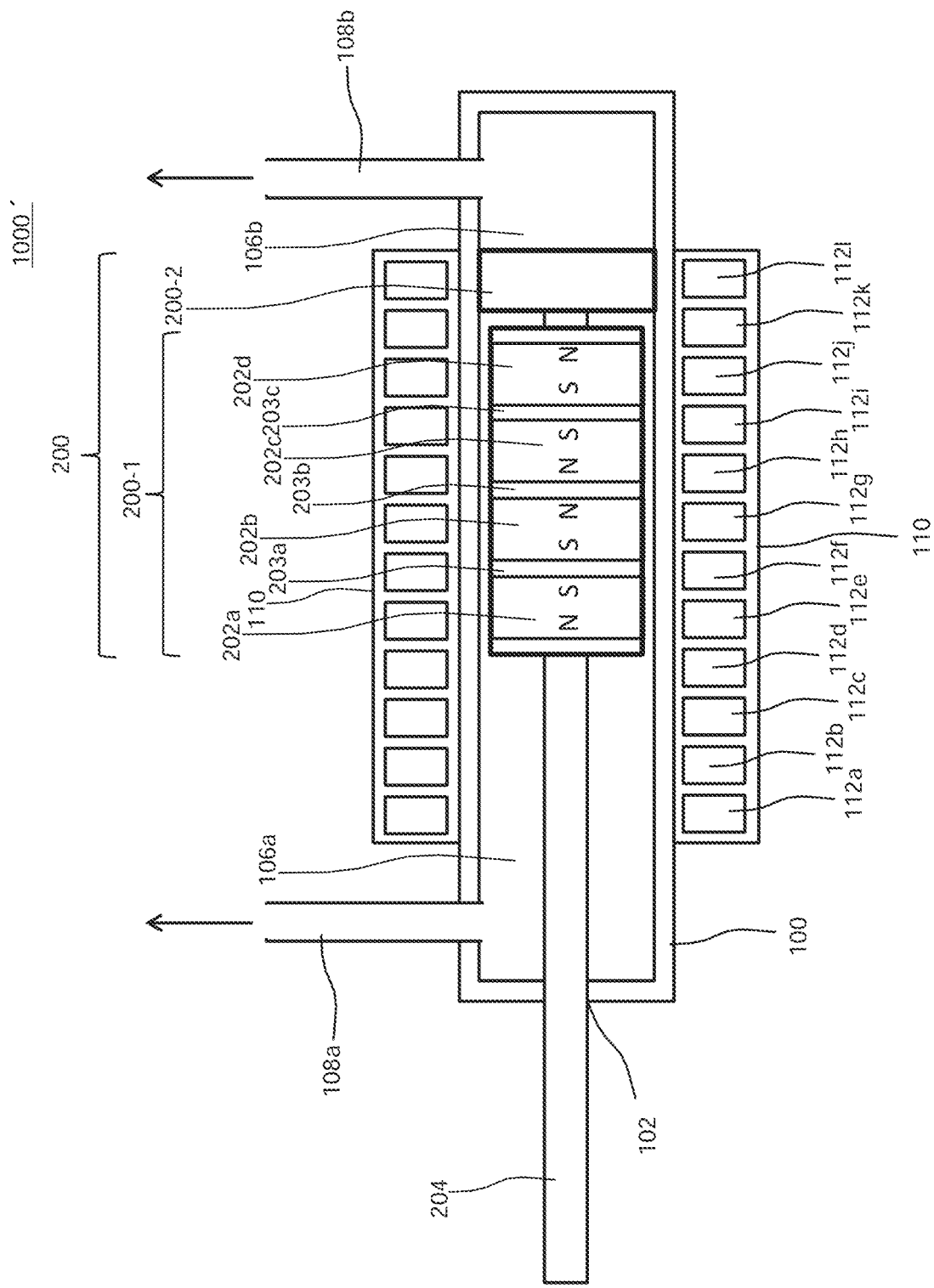

SINGLE PHASE DRIVE (a)

SOLENOID DRIVE (b)

(a)　　　　　　　　　(b)

SINGLE PHASE DRIVE

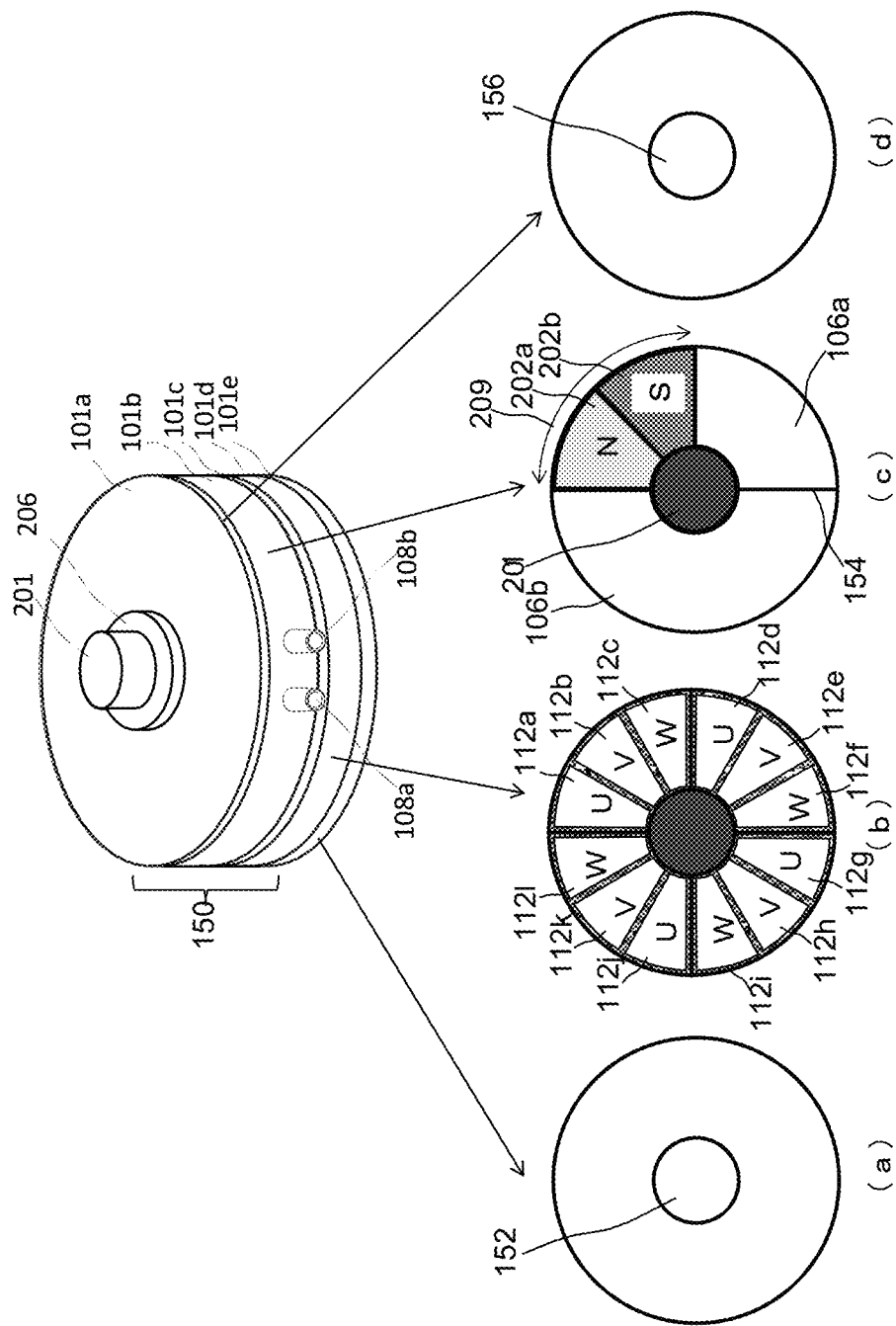

ACTUATOR DEVICE, HUMANOID ROBOT AND POWER ASSIST DEVICE

TECHNICAL FIELD

The present invention relates to an actuator device utilizing electromagnetic force and fluid pressure, as well as to a power assist device using the actuator, for supporting movement of a user.

BACKGROUND ART

Linear actuators utilizing electromagnetic force (linear motors) have been known and practically used in various fields (see, for example, Patent Literature 1).

Further, hybridization approaches of combining actuators of different types have been proposed and studied, such as actuators including combinations of a rotary electromagnetic motor, a voice coil motor or a ball screw with a working fluid actuator such as a McKibben type pneumatic actuator, an air cylinder or a vane motor (Non-Patent Literatures 1 to 3).

In addition, a technique of using an air spring in an electromagnetic actuator has been known in usages such as driving intake and exhaust valves of an engine. Specifically, in place of a mechanical spring used in an electromagnetic actuator, an air spring is used (see Patent Literature 2).

The combination of an air spring and an electromagnetic actuator here, however, is a technique assuming only a range of motion sufficient to enable opening/closing of a valve. Further, the object of an air spring is to alleviate shocks, by providing repulsive force when a movable body reaches the stroke end.

Meanwhile, there is an increasing demand for assist devices applying robotics techniques in many countries, including Japan, facing the concerns of fewer children and aging population. In the meantime, robots capable of maintaining balance or walking have been developed. By way of example, there is a robot capable of generating torques at various joints like a human being, by optimally distributing acting force necessary for movement to a plurality of any given contact points in a space (see Patent Literature 3).

Recently, development of robots assisting rehabilitation, such as exoskeleton robots aimed to assist lower limb/trunk movement has been strongly desired. An exoskeleton robot, for example, is used in rehabilitation of a patient suffering from spinal damage to promote self-reliant living (see Patent Literature 4).

Patent Literature 4 proposes a technique using a so-called "pneumatic-electric hybrid actuator," in which driving force of a motor and driving force of air muscle are coordinated, for a robot performing power-assisting of a user of such usage.

Further, Patent Literature 4 also discloses hybrid driving combining driving by a DC motor and air muscle for a robot manipulator.

There is also a proposal of a rotary actuator, which is an actuator for driving rotational motion, attaining both high torque performance in low heating and high responsiveness and high accuracy positioning controllability, by individually providing and juxtaposing a pneumatic actuator and an electromagnetic actuator and by driving these actuators in coordination (see Patent Literature 5).

Further, there is also a proposal of a piston engine capable of continuous rotation using pressurized air only or using air/fuel mixture (see Patent Literature 6).

CITATION LIST

Patent Literature

PTL 1: JP2011-214624A
PTL 2: JP2002-147209A
PTL 3: WO2007/139135
PTL 4: JP2012-045194A
PTL 5: JP2010-196777
PTL 6: U.S. Pat. No. 6,868,822

Non Patent Literature

NPL 1: James K. Mills, "Hybrid actuator for robot manipulators: design, control and performance," Proc. of ICRA1990, pp. 1872-1878 (1990)
NPL 2: H. Higo et al., "Dynamic Characteristic and Power Consumption on an Electro-Pneumatic Hybrid Positioning System," Proc. of the 6th JFPS International Symposium on Fluid Power, pp. 363-368 (2005)
NPL 3: YOSHIOKA et al., "A newly developed high torque and high precise indexing mechanism with hybrid-actuator," The 7th Manufacturing and Machine Tool Conference, pp. 207-208 (2008)
NPL 4: I. Sardelliti, J. Park, D. Shin and O. Khatib, "Air Muscle Controller Design in the Distributed Macro-Mini (DM2-) Actuation Approach," Proceedings of the 2007 IEEE/RSJ International Conference on Intelligent Robots and Systems San Diego, Calif., USA, Oct. 29-Nov. 2, 2007, WeB 2.1 p. 1822-1827

SUMMARY OF INVENTION

Technical Problem

If high output of such general electromagnetic actuators as described above is desired, the actuators must be made larger.

Further, conventional hybrid actuators have problems resulting from combination of two types of actuators using a link, a gear and the like. Specifically, depending on the mechanism used, responsiveness or robustness might be impaired, reduction in size might become difficult or range of motion might be limited.

If a conventional electromagnetic actuator is used for an application of an exoskeleton robot, for example, current excitation becomes necessary even for static force control such as gravity compensation, since actuator movement has high reversibility and, hence, heat generation becomes a problem.

The present invention was made to solve the above-described problems and its object is to provide a compact, high-output actuator device allowing force control.

Another object of the present invention is to provide a power assist device using the compact, high-output actuator device allowing force control.

Solution to Problem

According to an aspect, the present invention provides an actuator device, including: a fluid-tight housing configured to allow application of a fluid pressure from outside to inside; a movable element contained in the fluid-tight housing and slidable in accordance with the fluid pressure in the fluid-tight housing; a driving member for transmitting a driving force of the movable element to the outside of the fluid-tight housing; and a first magnetic member provided outside of the fluid-tight housing along a moving path of the movable element; wherein the movable element has a second magnetic member and is moved relative to the first magnetic member by excitation of the first or second magnetic member; the fluid-tight housing has a first chamber defined as a space between a first inner surface of the fluid-tight housing and one side surface of the movable element, and a second chamber defined as a space between a second inner surface of the fluid-tight housing and the other side surface of the movable element; the actuator device further including: fluid pressure supplying means for supplying the fluid pressure to each of the first and second chambers; wherein the fluid pressure supplying means controls supply of the fluid pressure such that the movable element is driven in the same direction as a direction of relative movement of the movable element caused by excitation of the first or second magnetic member.

Preferably, the fluid-tight housing is a cylinder having first and second ends in its axial direction; the first and second inner surfaces are cylinder inner surfaces at the first and second ends; the movable element includes a piston slidable in the cylinder; and the driving member transmits reciprocating motion of the piston to the outside of the cylinder.

Preferably, the first magnetic member is an electromagnetic coil member provided on an outer circumference of the cylinder; and the electromagnetic coil member is excited for the relative movement of the movable element.

Preferably, the electromagnetic coil member has a plurality of coils to be independently excited, provided over a prescribed width on the outer circumference of the cylinder; the second magnetic member includes a plurality of permanent magnets, and soft magnetic material is provided between each of the plurality of permanent magnets; and the permanent magnets are arranged to have opposite polarities alternately along the axial direction.

Preferably, the actuator device further includes: a control unit for controlling the fluid supplying means and excitation of the plurality of coils; wherein the control unit controls such that until a force generated by fluid pressure reaches a desired driving force, a force generated by electromagnetic force supplements the force generated by the fluid pressure.

Preferably, the actuator device further includes: a control unit for controlling the fluid supplying means and excitation of the plurality of coils; wherein the control unit controls excitation of the coils such that after a steady state is attained, deviation from a control target is compensated for.

Preferably, the fluid is a gas.

Preferably, the fluid is water or oil.

Preferably, the cylinder has a curved shape.

Preferably, the actuator device further includes an outer barrel provided to cover the cylinder and the first magnetic member; wherein the outer barrel has: an inlet for supplying a fluid of a prescribed fluid pressure to a fluid transmission path surrounded by the outer barrel and the cylinder; and an outlet for supplying, to the inlet of an actuator device of the same type, the fluid of the prescribed fluid pressure from the fluid transmission path; the actuator device further includes: a first control valve for selectively letting in the fluid in the fluid transmission path and supplying the fluid pressure to the first chamber, and for selectively discharging the fluid in the first chamber; and second control valve for selectively letting in the fluid in the fluid transmission path and supplying the fluid pressure to the second chamber, and for selectively discharging the fluid in the second chamber; wherein the fluid pressure supplying means controls the first and second control valves and thereby controls supply of the fluid pressure to the first and second chambers.

Preferably, the fluid-tight housing is a cylinder capable of keeping fluid-tight state; the driving member is an output shaft transmitting rotational motion of the movable element to the outside of the cylinder; the movable element is a rotor rotating integrally with the output shaft in the cylinder; a diaphragm extending from the output shaft to an inner circumference of the cylinder is provided in the cylinder; and the first and second inner surfaces are one surface and the other surface of the diaphragm.

Preferably, the first magnetic member is an electromagnetic coil member provided on a bottom surface side of the cylinder; and the electromagnetic coil member is excited for relative movement of the rotor.

Preferably, the electromagnetic coil member has a plurality of coils to be excited independently, provided in a circumferential direction on the bottom surface side of the cylinder; the second magnetic member includes a plurality of sector-shaped permanent magnets arranged adjacent to each other in the rotor; and the permanent magnets are arranged such that adjacent ones have opposite polarities alternately in the direction of the output shaft.

Preferably, the first magnetic member has a plurality of coils to be independently excited, provided along an outer circumference of the cylinder; the second magnetic member includes a plurality of sector-shaped permanent magnets arranged adjacent to each other in the rotor; and the permanent magnets are arranged to have opposite polarities alternately in the normal direction of the output shaft.

Preferably, the movable element is a rotor continuously rotating in the fluid-tight housing; a cross-section perpendicular to the rotation axis of the rotor is a curve of constant width having a plurality of vertexes; the fluid-tight housing has a cylindrical shape capable of maintaining fluid-tight state, and an inner surface of the cylindrical shape has a shape allowing the curve of constant width to rotate therein while being in contact therewith; the driving member is an output shaft transmitting the continuous rotational motion of the movable element to the outside of the fluid-tight housing; the first side surface is a part of a side surface of the rotor from a first contact portion at which the rotor and the inner surface of the fluid-tight housing are in contact to a second contact portion next to the first contact portion; and the second side surface is a part of a side surface of the rotor from a third contact portion at which the rotor and the inner surface of the fluid-tight housing are in contact to a fourth contact portion next to the third contact portion, and different from the first side surface.

Preferably, the first magnetic member is an electromagnetic coil member provided on a bottom surface side of the fluid-tight housing; and the electromagnetic coil member is excited for relative movement of the rotor.

Preferably, the first magnetic member is an electromagnetic coil member provided along an outer circumference of the fluid-tight housing; and the electromagnetic coil member is excited for relative movement of the rotor.

According to another aspect, the present invention provides a humanoid robot of which skeleton is driven by the above-described actuator device.

According to a further aspect, the present invention provides a power assist device for assisting musculoskeletal movement of a human as an object, including: an actuator device provided for each joint as an object of assisting, for generating force to assist movement of the joint; wherein the actuator device includes: a cylinder having first and second ends; an electromagnetic coil member provided over a prescribed width on an outer circumference of the cylinder; and a movable element housed in the cylinder and slidable as a piston in the cylinder; the movable element has a magnetic member and is moved relative to the electromagnetic coil member by excitation of the electromagnetic coil member. The actuator device further includes fluid supplying means for supplying a fluid to a first chamber defined as a space between the first end of the cylinder and one end of the movable element and to a second chamber defined as a space between the second end of the cylinder and the other end of the movable element. The power assist device further includes driving means for driving the actuator device, and when the movable element is to be relatively moved by excitation of the electromagnetic coil member, the driving means controls supply of the fluid such that the movable element is driven in the same direction by the fluid supplying means.

According to a still further aspect, the present invention provides a power assist device for assisting musculoskeletal movement of a human as an object, including: an actuator device provided for each joint as an object of assisting, for generating force to assist movement of the joint; wherein the actuator device includes: a cylindrical fluid-tight housing configured to allow application of fluid pressure from outside to inside; an output shaft transmitting driving force generated in the fluid-tight housing to the outside of the fluid-tight housing; a movable element housed in the fluid-tight housing, slidable in the fluid-tight housing in accordance with the fluid pressure and rotating integrally with the output shaft in the fluid-tight housing; a diaphragm extending from the output shaft to an inner circumference of the cylinder in the fluid-tight housing; and a first magnetic member provided outside the fluid-tight housing along a moving path of the movable element. The movable element has a second magnetic member and is moved relative to the first magnetic member by excitation of the first or second magnetic member; the fluid-tight housing has a first chamber defined as a space between one surface of the diaphragm in the fluid-tight housing and one end of the movable element, and a second chamber defined as a space between the other surface of the diaphragm and the other end of the movable element. The actuator device further includes fluid pressure supplying means for supplying the fluid pressure to each of the first and second chambers. The power assist device further includes driving means for driving the actuator device, and the driving means controls supply of the fluid such that when the movable element is moved relatively by the excitation, the movable element is driven in the same direction by the fluid supplying means.

Advantageous Effects of Invention

The actuator device and the power assist device of the present invention are compact and high-output, and allow highly responsive force control.

BRIEF DESCRIPTION OF DRAWINGS

FIG. 10 illustrates a cross-sectional structure of a pneumatic-electric hybrid actuator device 1000' in accordance with a modification of Embodiment 1.

FIG. 22 includes schematic illustrations showing inside of a stator 150.

DESCRIPTION OF EMBODIMENTS

Figure 1:
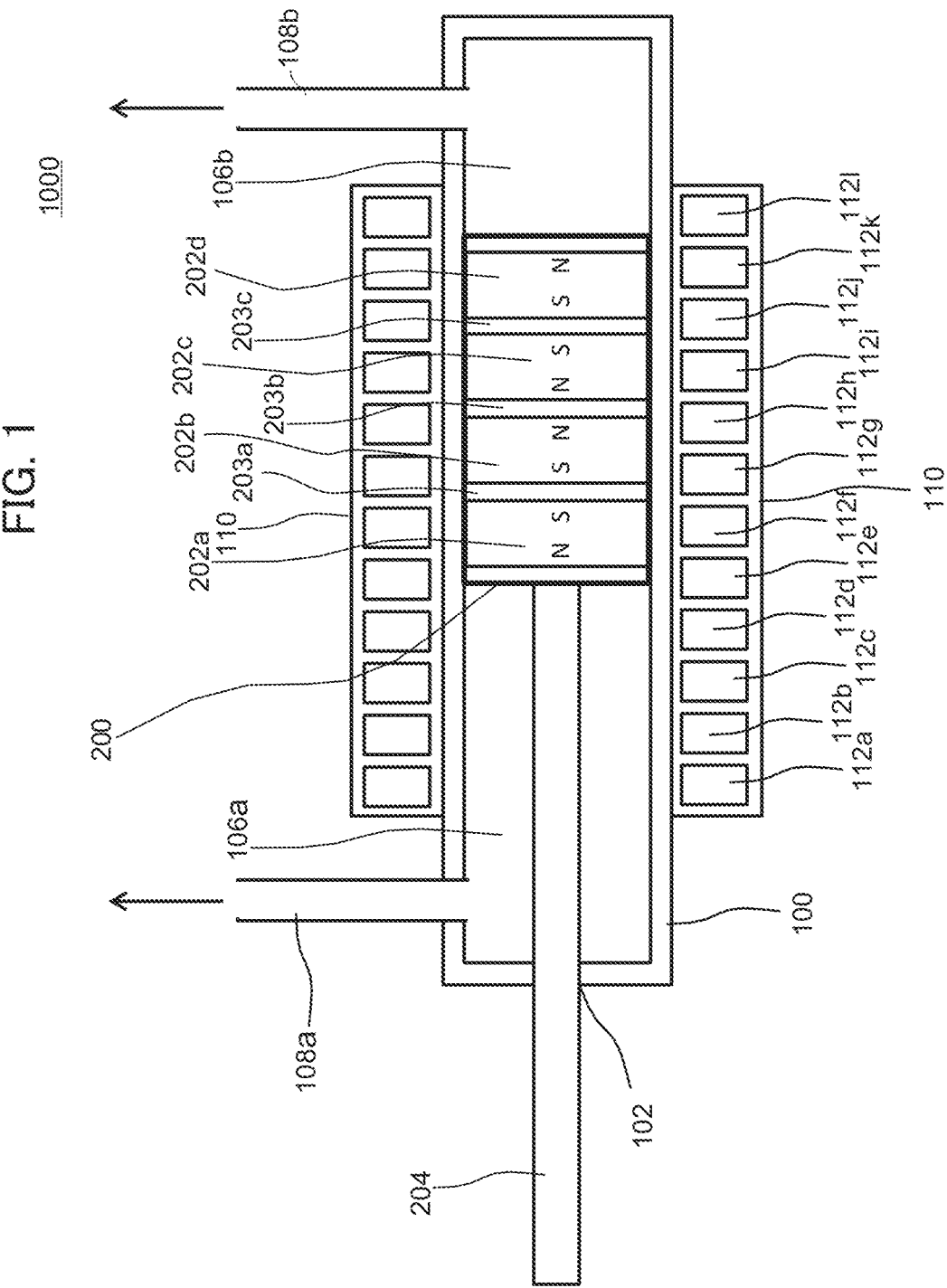
FIG. 1 is an illustration showing a cross-sectional structure of a pneumatic-electric hybrid actuator device 1000 in accordance with an embodiment of the present invention.

In the following, structures of pneumatic-electric hybrid actuator devices in accordance with embodiments of the present invention will be described with reference to the drawings. In the embodiments described below, the components and process steps denoted by the same reference characters are the same or corresponding components or steps and, therefore, description thereof will not be repeated unless necessary.

In the following description, by way of example, the fluid for driving the actuator is air.

Embodiment 1

FIG. 1 is an illustration showing a cross-sectional structure of a pneumatic-electric hybrid actuator device 1000 in accordance with an embodiment of the present invention.

Figure 2:
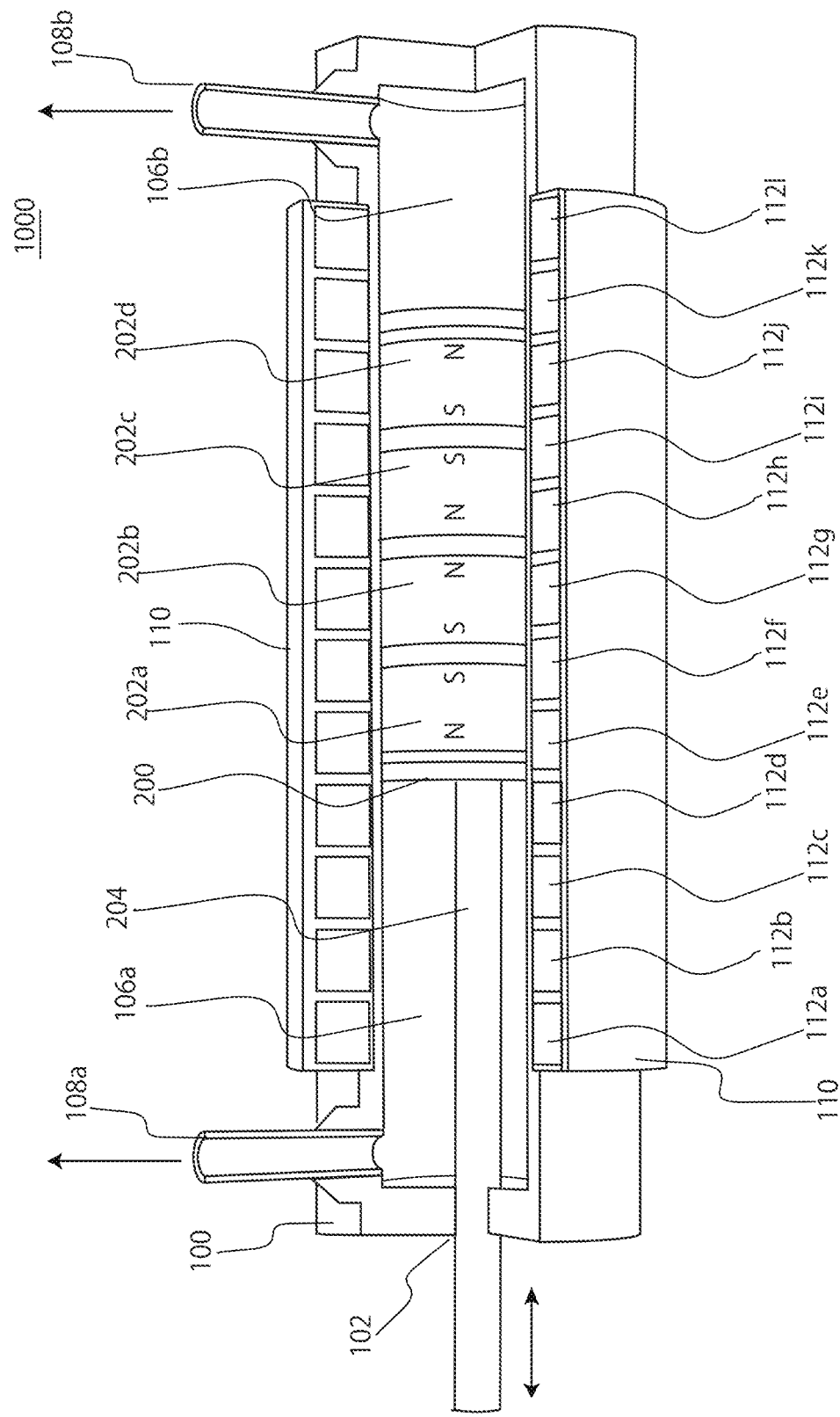
FIG. 2 is a perspective view of pneumatic-electric hybrid actuator device 1000 with one-fourth of an upper front side of its cylinder removed to show its internal structure.

FIG. 2 is a perspective view of pneumatic-electric hybrid actuator device 1000 with one-fourth of an upper front side of its cylinder removed to show its internal structure.

With reference to FIGS. 1 and 2, pneumatic-electric hybrid actuator device 1000 includes a cylinder 100 and a movable element 200 slidably accommodated in cylinder 100.

Cylinder 100 functions as a movable guide portion of an electromagnetic actuator and as a cylinder of a pneumatic actuator. Movable element 200 functions as a movable element of the electromagnetic actuator and as a piston of the pneumatic actuator. Specifically, in pneumatic-electric hybrid actuator device 1000, the movable element as an element transmitting the electromagnetic interaction to an output shaft and a moving space of the movable element are integrated with the piston as an element transmitting air pressure to the output shaft and a moving space of the piston, respectively.

On an outer circumference of cylinder 100, an electromagnetic coil member 110 is provided, arranged over a prescribed width along the axial direction of cylinder 100. Electromagnetic coil member 110 has a plurality of coils 112a to 112l in its inside. The plurality of coils 112a to 112l are excited in independent polarity directions by independently supplied currents, respectively. More specifically, the plurality of coils 112a to 112l are configured such that AC currents of mutually different phases flow therethrough. For example, the plurality of coils 112a to 112l may be divided to three groups, and alternative currents with phase shifted by (2π/3) from each other (symmetrical three-phase AC) are caused to flow through respective groups, to apply thrust to movable element 200. The alternative current or currents applied to electromagnetic coil member 110 is not limited to such "symmetrical three-phase AC" and any current may be used provided that it can drive the movable element.

Further, in each space between the plurality of coils 112a to 112l, soft magnetic material is interposed as shown in the figure. Thus, lines of magnetic force concentrate on the soft magnetic material and magnetic force can be enhanced. Here, interposition of soft magnetic material is not absolutely necessary. If the soft magnetic material is not interposed, pulsation of thrust is advantageously avoided when no current is caused to flow, though the thrust becomes lower.

Further, the coils are surrounded by a casing of soft magnetic material. Because of this structure, magnetic flux that has passed through the coil/soft magnetic material passes through the casing and goes back to the movable element again. The casing prevents leakage of magnetic flux to the environment and improves thrust.

At one end of cylinder 100, an opening 102 is provided at the center, and an output shaft 204 connected to movable element 200 is inserted through opening 102. Output shaft 204 transfers to the outside the driving force generated by the driving of movable element 200. Opening 102 and output shaft 204 are formed to have a sealed structure that allows sliding and tight-sealing of fluid (air).

Movable element 200 has, on a side facing the surface connected to output shaft 204, a plurality of magnetic members 202a to 202d arranged opposite to the plurality of coils 112a to 112l, and by excitation of the plurality of coils 112a to 112l, and movable element 200 moves relative to electromagnetic coil member 110.

Here, "magnetic member" may be any member that generates driving force in response to the magnetic force from the coils. Though it is typically a permanent magnet, any member formed of magnetic material may be used. In the following description, it is assumed that the "magnetic member" is a permanent magnet, unless specified otherwise.

Magnetic members 202a to 202d are arranged to have opposite polarities alternately. Thus, movable element 200 and the plurality of coils 112a to 112l form a linear motor.

Figure 3:
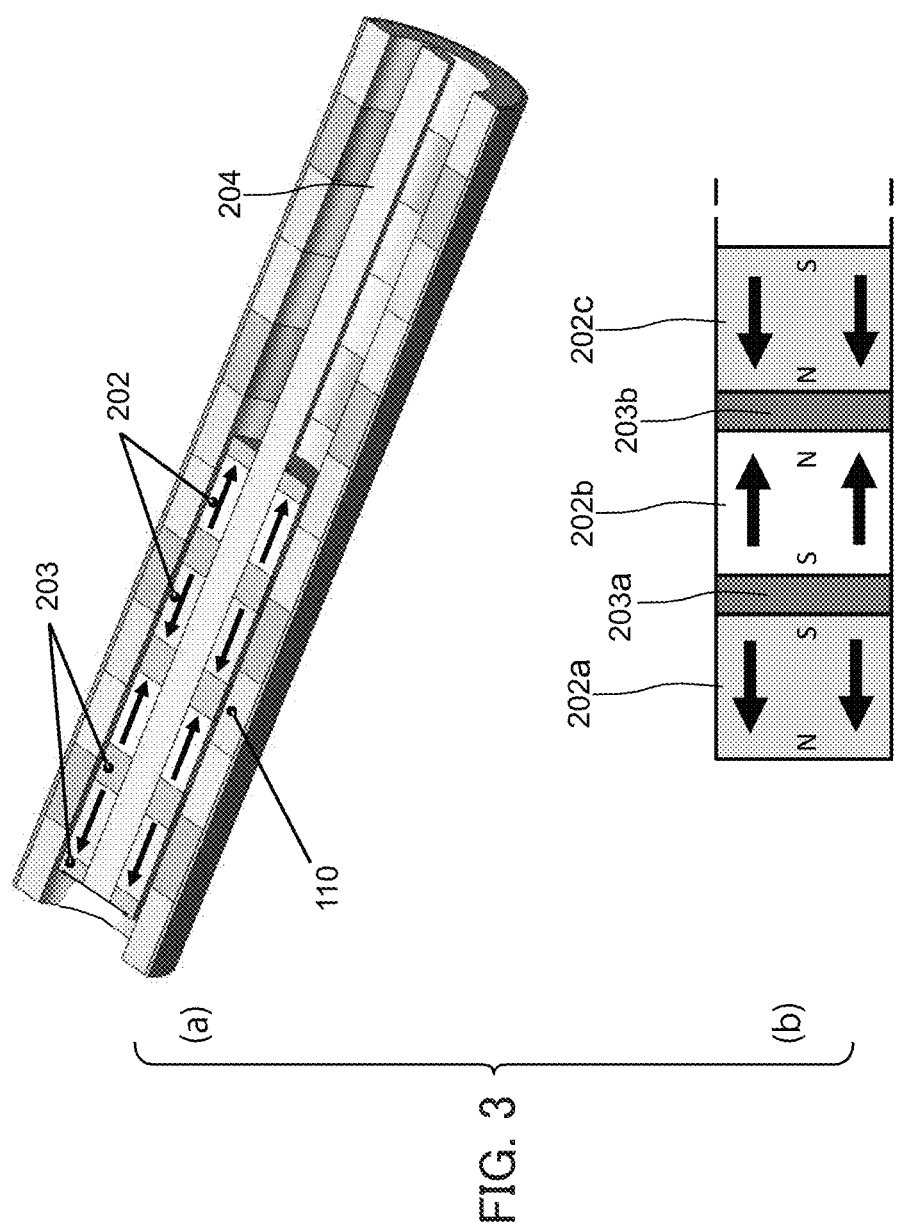
FIG. 3 shows arrangement of magnetic members 202 in a movable element 200.

FIG. 3 illustrates arrangement of magnetic members 202 in movable element 200.

Magnetic members 202a to 202d will be collectively referred to as magnetic members 202.

In addition to FIGS. 1 and 2, FIGS. 3(a) and 3(b) show that intermediate members 203a to 203c are arranged interposed between magnetic members 202a to 202d having opposite polarities. Intermediate members 203a to 203c are of soft magnetic material having higher magnetic permeability than the permanent magnets of magnetic members 202a to 202d. Since the magnetic permeability is higher than the permanent magnets, magnetic flux of opposing permanent magnets comes to exit approximately perpendicularly from the intermediate member to the central axis of the movable element or comes to enter in that direction, being a magnetic field having magnetic flux density higher than when only the permanent magnets are used. Thus, the magnetic field intensity can be increased at a position of electromagnetic coil member 110.

Further, such a structure makes it easier to form all of the intermediate members 203a to 203c and the magnetic members (permanent magnets) 202a to 202d as disk-shaped or ring-shaped components having the same radius. Further, by adjusting thickness of intermediate members 203a to 203c and magnetic members (permanent magnets) 202a to 202d, high magnetic flux density can easily be realized.

Details of a structure for driving a linear motor as such are disclosed, for example, in Japanese Patent No. 5422175.

The structure for driving a linear motor may be a structure for a "linear vernier motor" as described, for example, in JP2012-244688A.

A chamber 106a is a space between one end of cylinder 100 and one end surface of movable element 200 connected to output shaft 204. A chamber 106b is a space between the other end of cylinder 100 and the other end surface of movable element 200. Air of a prescribed pressure is supplied to or air is discharged from chamber 106a, through a duct 108a having a control valve. Air of a prescribed pressure is supplied to or air is discharged from chamber 106b, through a duct 108b *having a control valve.*

The above-described driving of the linear motor and supply/discharge of air to/from chambers 106a and 106b are controlled by a control unit, not shown. When the movable element is to be driven to a target direction, control unit controls supply/discharge of air such that driving force for driving movable element 200 in the same direction as the direction of relative movement of movable element 200 is caused by excitation of the plurality of coils 112a to 112l.

Though FIGS. 1 to 3 show, as an example, a structure in which output shaft 204 is provided on one side of cylinder 100 only, the structure may have output shafts 204 on opposite ends of movable element 200 being protruded to the outside from opposite ends of cylinder 100.

Further, the fluid is not limited to a gas such as compressed air, and water, oil or magnetic fluid actuator may be used for the application. When water or oil is used, coil cooling efficiency can be improved, and when magnetic fluid is used, viscosity control becomes possible as a hardware characteristic.

Figure 4:
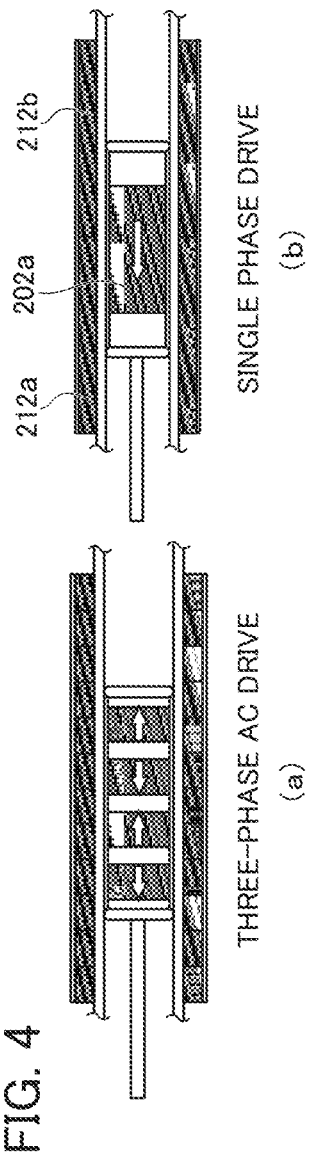
FIG. 4 illustrates methods of driving an electromagnetic actuator.

FIG. 4 illustrates methods of driving an electromagnetic actuator.

In the description with reference to FIGS. 1 to 3, by way of example, symmetric three-phase alternate currents are applied as alternate currents to electromagnetic coil member 110. FIG. 4(a) shows driving with such three-phase alternate currents.

On the other hand, as shown in FIG. 4(b), movable element 200 may have one magnetic member 202a, and electromagnetic coil member 110 may have coils 212a and 212b connected in series with their winding direction reverse to each other, so that the resulting structure can be driven with single phase.

Figure 5:
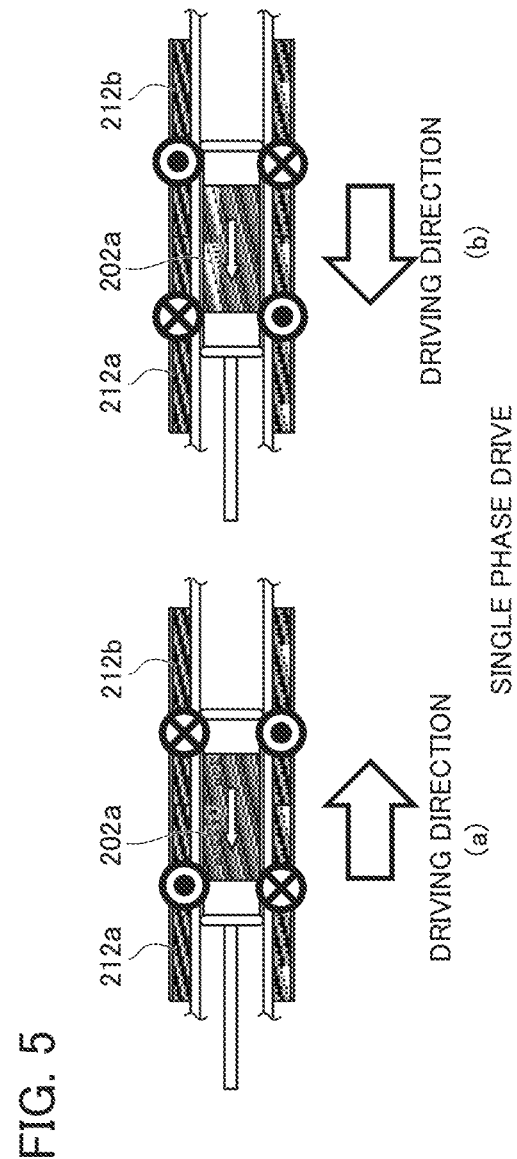
FIG. 5 illustrates coil current in single-phase driving.

FIG. 5 illustrates coil currents in single-phase driving in the example of FIG. 4(b).

In FIGS. 5(a) and 5(b), a cross sign (a cross in a circle) indicates a current flowing from the front surface to the rear surface of the paper and a dot sign (a black circle in a white circle) indicates a current flowing from the rear surface to the front surface of the paper.

As shown in FIG. 5(a), when a current is caused to flow to coils 212a and 212b for driving in a single phase, the movable element is driven in the right direction, and when the current direction is reversed as shown in FIG. 5(b), the movable element is driven in the left direction.

Figure 6:
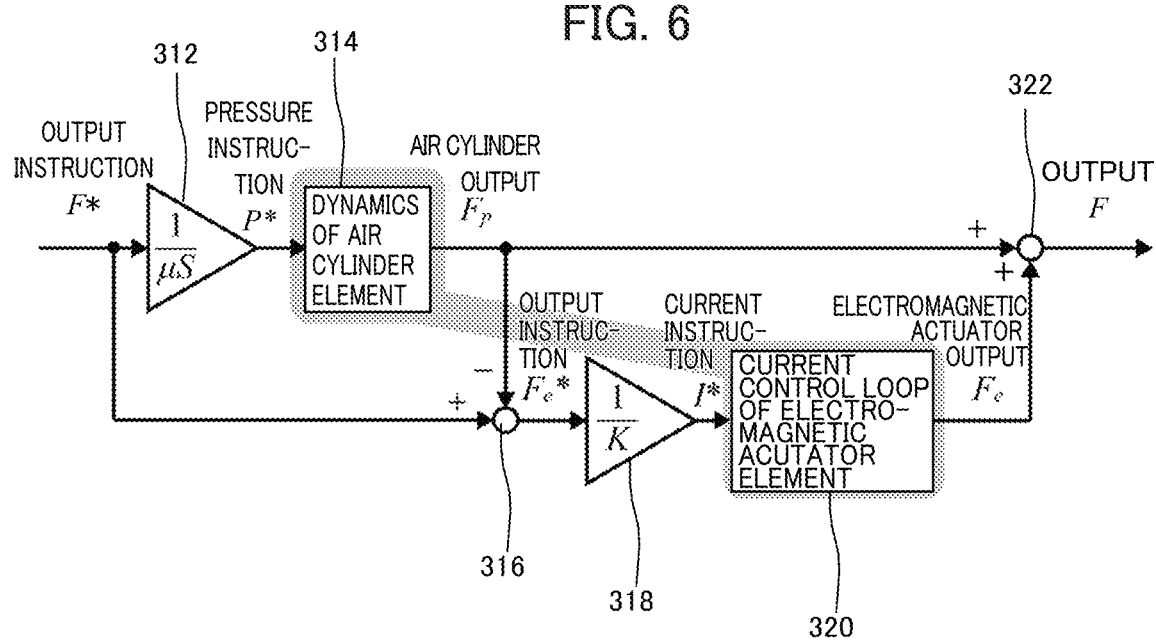
FIG. 6 is a functional block diagram illustrating an example of control structure of a control unit.

FIG. 6 is a functional block diagram illustrating an example of control structure of a control unit.

FIG. 6 is a functional block diagram of the control unit when force control is effected such that the force generated on the output shaft attains to a target magnitude.

It is noted that, by measuring a relation between pressure instructions and outputs beforehand, an output from an air cylinder can be calculated based on the measurements. By way of example, an output of an air cylinder can be estimated by subtracting friction from pressure in the cylinder.

Referring to FIG. 6, the control unit includes an amplifier 312 receiving, as an output instruction, a target output (force) F*, converting it at a prescribed gain (1/μS) and generating a pressure instruction P* for the pressure to be supplied to cylinder 100.

Here, S represents cross-sectional area of the cylinder and μ represents efficiency of air cylinder element.

The control unit further includes: a difference element 316 providing a difference between an air cylinder output (force) Fp output from air cylinder element 314 in accordance with the pressure instruction P* and the output instruction F*; an amplifier 318 converting an output instruction Fe* as an output from difference element 316 at a prescribed gain (1/K) and thereby generating a current instruction I* representing a current value for driving the linear motor; and a current control loop 320 controlling the electromagnetic actuator. The pneumatic-electric hybrid actuator device generates, as a final output F, a combination of air cylinder output (force) Fp and electromagnetic actuator output (force) Fe. Here again, K represents thrust constant of electromagnetic actuator element.

It is noted that the force generated by the electromagnetic actuator is in proportion to the excitation currents and, therefore, what is necessary is only the current control. There may be pulsation of force, however, that generates even without current excitation. In that case, such pulsation may be modeled in advance and may be added as a correction value to the instruction current.

Figure 7:
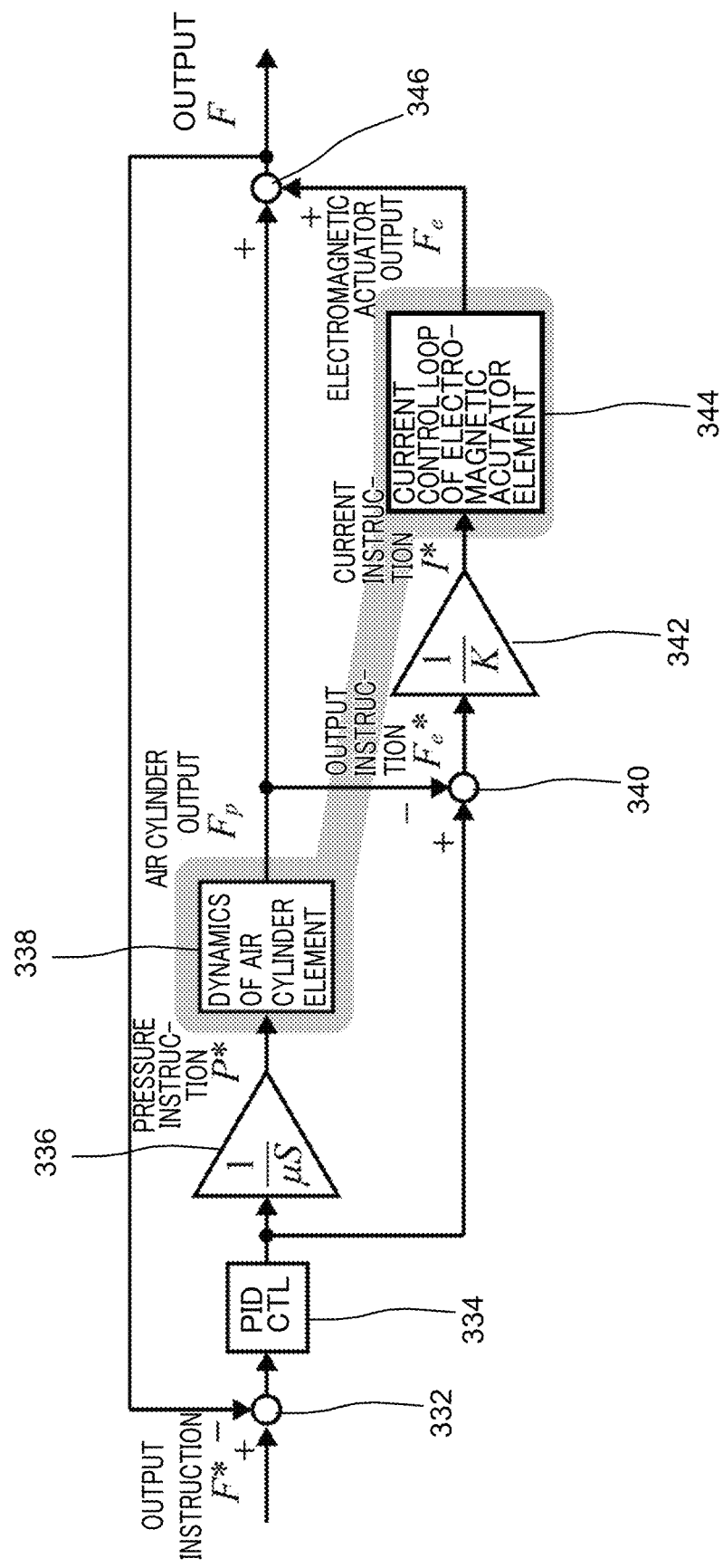
FIG. 7 is a functional block diagram illustrating another example of control structure of the control unit.

FIG. 7 is a functional block diagram illustrating another example of control structure of the control unit.

FIG. 7 is also a functional block diagram of the control unit when force is controlled such that the force generated on the output shaft attains to a target magnitude. What is different from the configuration of FIG. 6 is that the final output F is fed back to the input side.

As in the example of FIG. 6, the output from air cylinder may be calculated based on the relation between the pressure instructions and the outputs measured beforehand. It is assumed that a sensor for measuring the final output F is provided. A load cell, for example, may be used as such a sensor.

Referring to FIG. 7, the control unit receives the target output (force) F* as an output instruction, causing a difference element 332 to find the difference from the final output (force) F, and to input the output of difference element 332 to a PID control unit 334, where an amplifier 336 converts the output of PID control unit 334 at a prescribed gain (1/μS) and thereby generates a pressure instruction P* for the pressure to be supplied to cylinder 100. Here again, S represents the cross sectional area of the cylinder, and μ represents efficiency of air cylinder element.

The control unit further includes: a difference element 340 providing a difference between the output instruction F* and an air cylinder output (force) Fp output from air cylinder element 338 in accordance with the pressure instruction P*; an amplifier 342 converting an output instruction Fe* as an output from difference element 340 at a prescribed gain (1/K) and thereby generating a current instruction I* representing a current value for driving the linear motor; and a current control loop 344 controlling the electromagnetic actuator. The pneumatic-electric hybrid actuator device generates, as a final output F, a combination of air cylinder output (force) Fp and electromagnetic actuator output (force) Fe. Here again, K represents thrust constant of electromagnetic actuator element.

By such a configuration also, effects similar to those attained by the example of FIG. 6 can be attained.

Figure 8:
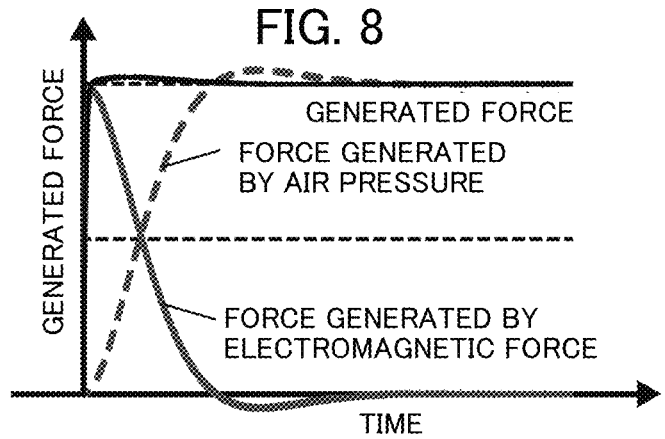
FIG. 8 shows change of force over time generated under the control of FIG. 7.

FIG. 8 shows change of force over time generated under the control of FIG. 6 or FIG. 7.

When control such as shown in FIG. 6 or FIG. 7 is done, it becomes possible, as shown in FIG. 8, to supplement the force (driving power) generated by air pressure with force generated from the linear motor by electromagnetic force, until the force generated by air pressure, which has low responsiveness, reaches the desired driving force.

Specifically, in actuator device 1000, for force control, in order to improve delay in air pressure control, the difference between the overall target output of hybrid actuator device and the output by the air cylinder element is used as an output instruction, so as to adjust the output of electromagnetic actuator having a response time shorter than air pressure control. After sufficient time, the output of air cylinder element becomes stable and, therefore, the electromagnetic actuator element serves only to immediately respond to the change in output of air cylinder element caused by disturbance. As a result, necessary coil excitation current is small and heat generation can be reduced. Even after the steady state is attained, it is possible to use output of electromagnetic actuator having a response time shorter than air pressure control to compensate for deviation from the target of control.

Specifically, when an external force is applied after the steady state is attained and the pressure sensor value of air cylinder changes, the output instruction to the electromagnetic actuator changes and the output of electromagnetic actuator changes immediately.

As a result, in actuator device 1000, even in force control, the mechanism for generating electromagnetic driving force and the mechanism for generating air pressure driving force are integrated, and thereby reduction in size and high output with good time responsiveness can both be realized.

Figure 9:
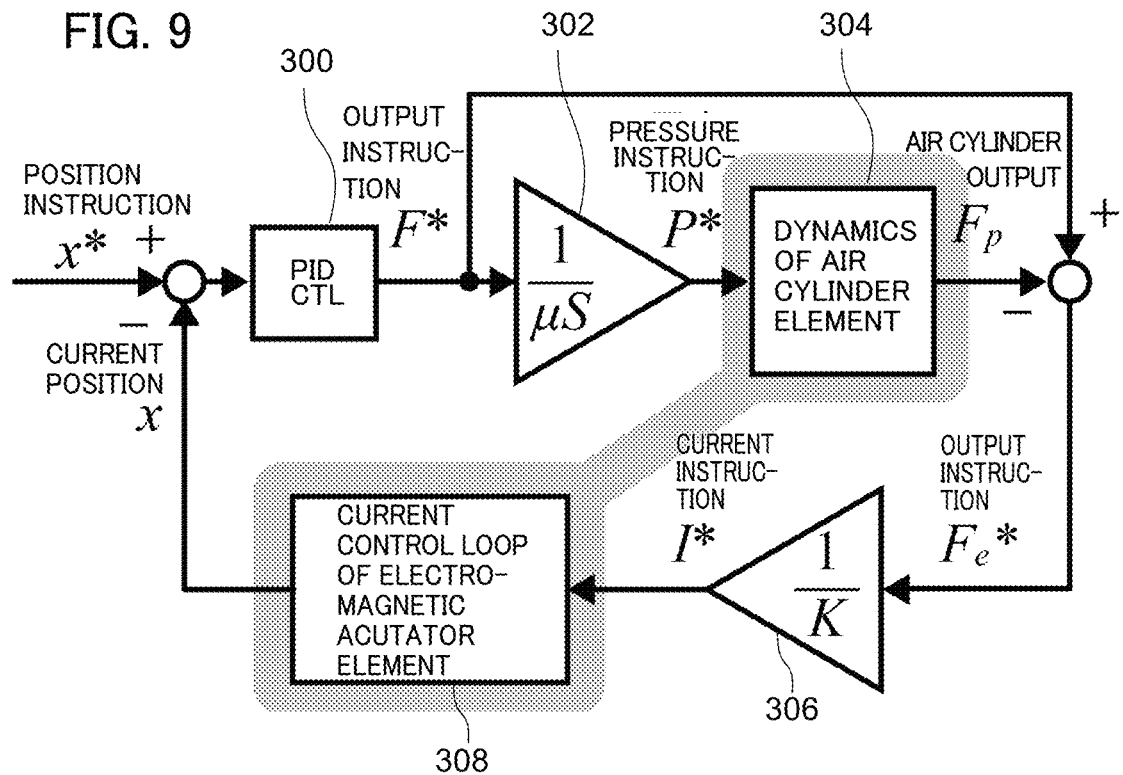
FIG. 9 is a functional block diagram illustrating still another example of control structure of the control unit.

FIG. 9 is a functional block diagram illustrating still another example of control structure of a control unit.

FIG. 9 is a functional block diagram of the control unit for position control such that the position of output shaft reaches a target position.

Here, it is assumed that the position of movable element 200 is detected, for example, by a sensor detecting the position of output shaft 204. A magnetic sensor using a Hall element, an optical sensor using a plate with slits or the like may be used as the sensor.

Referring to FIG. 9, the control unit includes: a PID control unit 300 generating the output instruction F* instructing the target driving force by PID control based on the difference between the current position x of movable element 200 and a position instruction x* indicating the target position of driving; and an amplifier 302 converting the output instruction F* at a prescribed gain (1/µS) and thereby generating a pressure instruction P* for the pressure to be supplied to cylinder 100.

Here, S represents cross-sectional area of the cylinder and u represents efficiency of air cylinder element.

The control unit further includes: an amplifier 306 converting the output instruction Fe* which is a difference between an air cylinder output (driving force) Fp output from air cylinder element 304 in accordance with the pressure instruction P* applied to movable element 200 in cylinder 100 and the output instruction F*at a prescribed gain (1/K) and thereby generating a current instruction I* representing a current value for driving the linear motor; and a current control loop 308 controlling the electromagnetic actuator. Here, K represents thrust constant of electromagnetic actuator element.

Specifically, in actuator device 1000, for position control, in order to improve delay in air pressure control, the difference between the overall target output of hybrid actuator device and the output by the air cylinder element is used as an output instruction, so as to adjust the output of electromagnetic actuator having a response time shorter than air pressure control. After sufficient time, the output of air cylinder element becomes stable and, therefore, the electromagnetic actuator element serves only to immediately respond to the change in output of air cylinder element caused by disturbance. As a result, necessary coil excitation current is small and heat generation can be reduced. Even after the steady state is attained, it is possible to use output of electromagnetic actuator having higher time responsiveness than air pressure control to compensate for deviation from the target of control.

As a result, in actuator device 1000, the mechanism for generating electromagnetic driving force and the mechanism for generating air pressure driving force are integrated, and thereby reduction in size and high output with good time responsiveness can both be realized.

Modification of Embodiment 1

In hybrid actuator device 1000 shown in FIG. 1, in movable element 200, a plurality of magnetic members 202a to 202d and intermediate members 203a to 203c also function as a piston sliding over the inner surface of cylinder 100.

FIG. 10 is an illustration showing a cross-sectional structure of a pneumatic-electric hybrid actuator device 1000' in accordance with a modification of Embodiment 1.

In FIG. 10, the plurality of magnetic members 202a to 202d and the intermediate members 203a to 203c will be collectively referred to as magnetic members 200-1.

As shown in FIG. 10, in movable element 200, a piston 200-2 sliding over the inner surface 100 may be provided separately, and the chambers 106a and 106b may be divided by piston 200-2. In this structure, there may be a space between the inner surface of cylinder 100 and the plurality of magnetic members 202a to 202d and the intermediate members 203a to 203c.

(Power Assist Device)

Next, description will be given on a structure of a power assist device using the above-described actuator device 1000 as an actuator for driving joints of an exoskeleton robot.

Specifically, in the embodiment below, an exoskeleton robot using the hybrid actuator for walking/posture rehabilitation will be described.

It is noted that the hybrid exoskeleton robot of the present invention can be used not only for an exoskeleton robot for assisting movements of lower limbs but also for an exoskeleton robot for assisting movements of upper limbs.

Though an exoskeleton robot assisting movements of lower limbs as a pair will be described below, it may also be used as an exoskeleton robot for assisting movements of one of the lower limbs, or one of the upper limbs.

Further, the hybrid exoskeleton robot of the present invention is not limited to assisting movements of at least "one of the lower limbs, or one of the upper limbs" as described above, and it may assist any musculoskeletal movement of a human as an object. For instance, it may assist only the movement of hips of the human as an object, or it may assist the movement of hips in connection with the movement of lower limbs when one is walking or running. In the present specification, assists for the human movements as the object will be generally referred to as "assist of musculoskeletal movement of a human as an object."

The exoskeleton robot in accordance with an embodiment has an exoskeleton. The "exoskeleton" means a skeletal structure of the robot that corresponds to the skeletal structure of a human. Specifically, the "exoskeleton" refers to a frame (framework) supporting from outside part of the body of the human who wears the exoskeleton robot.

The frame structure is further provided with joints for moving each part of the frame structure in accordance with movements based on the human skeletal structure.

Particularly, an exoskeleton robot assisting movements of lower limbs has a base and a lower body with joints of active six degrees of freedom at positions corresponding to ankles, knees and left and right hips. The six joints are driven by artificial muscles implemented by pneumatic-electric hybrid actuators. In the following, a joint driven by an actuator for exerting support force for a joint of the user in the exoskeleton robot will be referred to as an "active joint."

Figure 11:
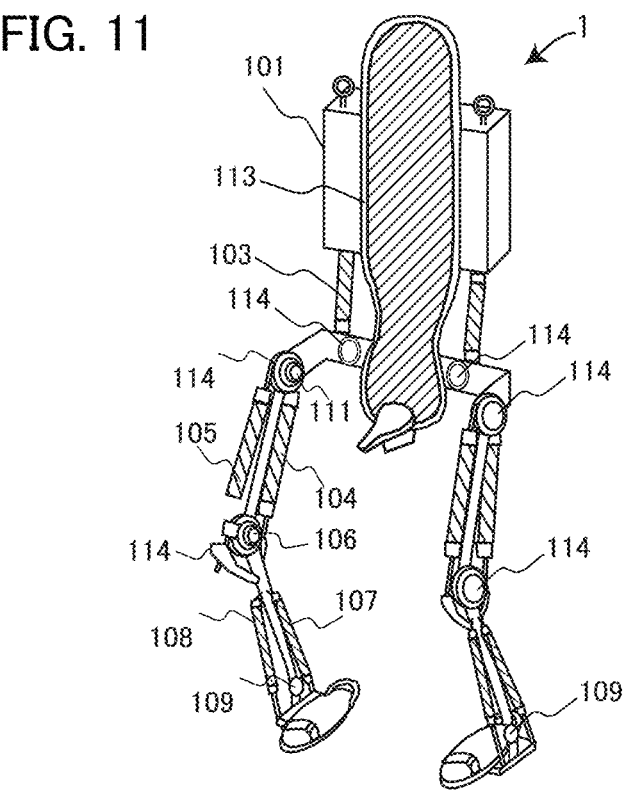
FIG. 11 shows a structural example of an exoskeleton robot 1 in accordance with an embodiment of the present invention.

FIG. 11 shows a structural example of an exoskeleton robot 1 in accordance with an embodiment of the present invention. This exoskeleton robot 1 has ten degrees of freedom.

Regarding such a structural example of exoskeleton robot, a similar structure is disclosed in Patent Literature 3 mentioned above.

Referring to FIG. 11, exoskeleton robot 1 includes: frame structures corresponding to two legs; a backpack 101; a soft sheet 113; HAA antagonist muscles 103; HFE extensor muscles 104; HFE motors 111; KFE extensor muscles 105; KFE motors 106; AFE extensor muscles/AAA antagonist muscles 107; AFE flexor muscles 108; joints 109; and joints 114 provided on the frame structure.

Though backpack 101 is directly mounted on the structure for supporting movement in the example shown in FIG. 11, backpack 101 may be detached from this structure.

Backpack 101 contains a controller for controlling driving of the exoskeleton robot.

Further, an optical encoder, for example, is attached to the rotation shaft of joint 109 to measure a joint angle. Similarly, an optical encoder is attached also to joint 114. The optical encoder may be attached not on a shaft but on a belt wound around the shaft, and may be configured to read direction and distance of movement. The controller in backpack 101 controls driving of artificial muscle (actuator) in accordance with the read joint angle.

The encoder may be accommodated in the shaft.

Figure 12:
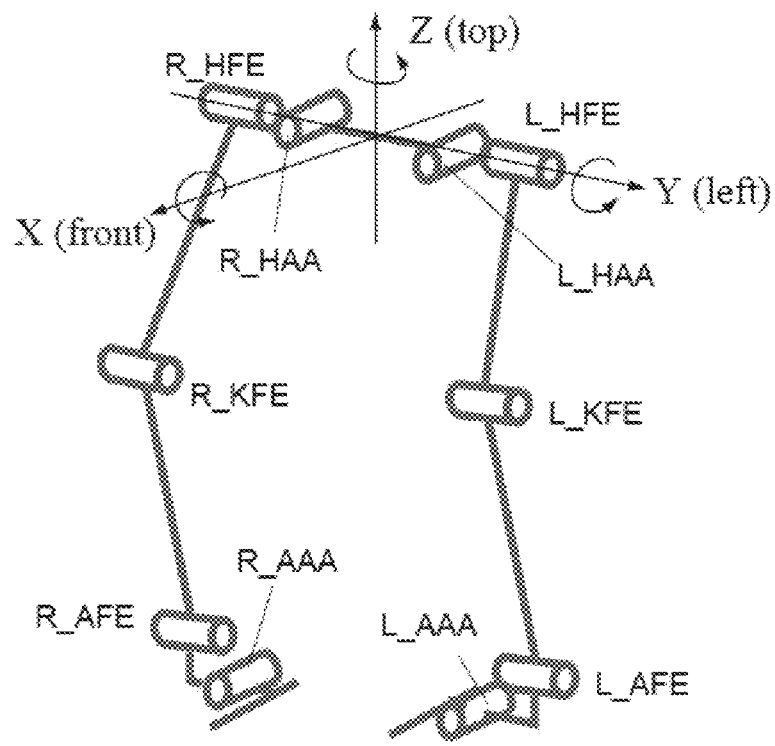
FIG. 12 shows a structure of degrees of freedom of exoskeleton robot 1.

FIG. 12 shows a structure of degrees of freedom of exoskeleton robot 1.

In FIG. 12, at each joint, the designation of "R_" indicates that it is a joint on the right side, and the designation "L_" indicates that it is a joint on the left side.

Referring to FIGS. 11 and 12, of ten degrees of freedom, the left and right AFE joints adopt antagonistic driving by extensors and flexors. Joints other than those driven antagonistically are passively driven. It is noted that more of the joints may be antagonistically driven.

In FIG. 11, on the torso part to which legs are connected, an attitude sensor is mounted to detect attitude of the base part. Further, a wire encoder (or motor encoder) is attached to every joint to enable the measurement of joint angle. A structure may also be possible in which target torque to be generated at each joint is calculated by detecting muscle potential of lower limbs in addition to the joint angles.

Further, on a sole part, a floor reaction force sensor may be mounted to determine whether or not the sole part expected to be in contact is actually in contact, or to assist modifying model error included in Jacobian matrix.

Further, a linear motor driver and a valve for air pressure control are contained in backpack 101 in addition to the controller.

Further, a battery, a compressed air tank (or $CO_2$ gas tank) and a regulator may be provided in backpack 101, so as to enable autonomous driving for a short period in case power line and air supply should fail.

Alternatively, backpack 101 may have a built-in battery and contain a compressor and a power source for driving motors.

Figure 13:
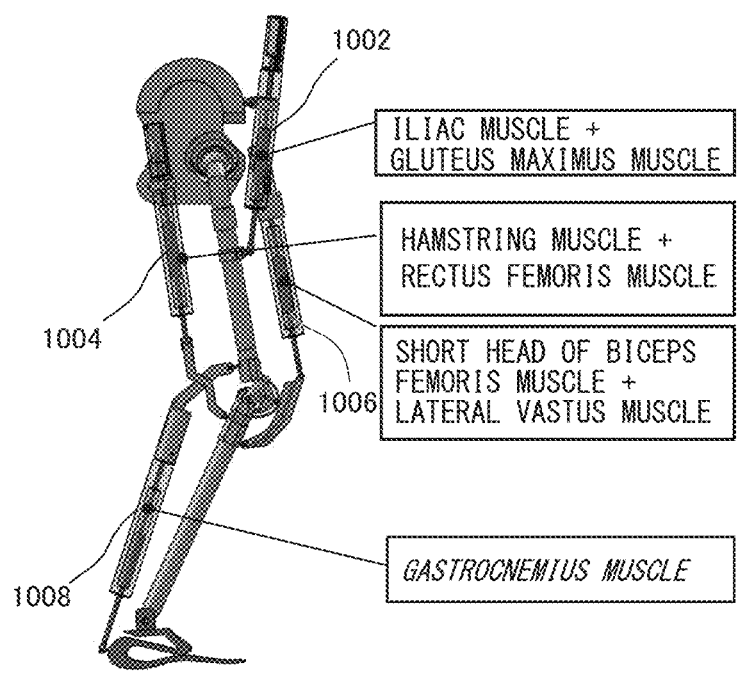
FIG. 13 shows another example of the arrangement of artificial muscles (actuator devices) on an exoskeleton robot for lower limbs.

FIG. 13 shows another example of the arrangement of artificial muscles (actuator devices) on an exoskeleton robot for lower limbs.

As shown in FIG. 13, as an artificial muscle for driving inflection of hip joint, an actuator device 1002 having a function corresponding to human "iliac muscle+gluteus maximus muscle" is provided on the skeleton.

Further, as an artificial muscle for driving inflection of hip joint and extension of knee joint, an actuator device 1004 having a function corresponding to human "hamstring muscle+rectus femoris muscle" is provided on the skeleton.

Further, as an artificial muscle for driving inflection of knee joint and extension of knee joint, an actuator device 1006 having a function corresponding to human "short head of biceps femoris muscle+lateral vastus muscle" is provided on the skeleton.

Further, as an artificial muscle for driving inflection of knee joint, an actuator device 1008 having a function corresponding to human "gastrocnemius muscle" is provided on the skeleton.

Figure 14:
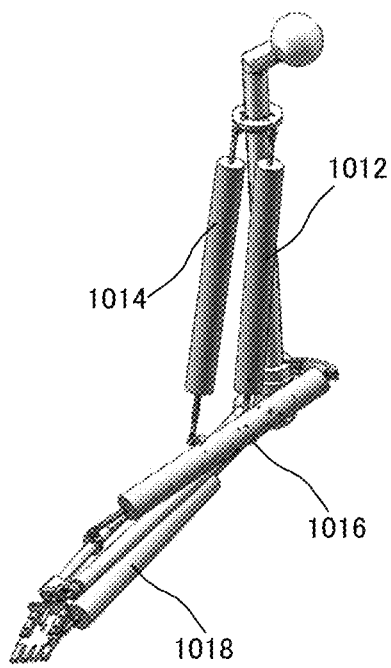
FIG. 14 shows an example of the arrangement of artificial muscles (actuator devices) on an exoskeleton robot for upper limbs.

FIG. 14 shows an example of the arrangement of artificial muscles (actuator devices) on an exoskeleton robot for upper limbs.

As shown in FIG. 14, as an artificial muscle for driving inflection and extension of elbow joint, an actuator device 1012 having a function corresponding to human "biceps brachii muscle+triceps brachii muscle" is provided on the skeleton.

Further, as artificial muscles for driving pivotal movement of forearm, actuator devices 1016 and 1018 having a function corresponding to human "brachioradial muscle" are provided on the skeleton.

With such a structure, an exoskeleton robot assisting movements of lower limbs or upper limbs of a human being can be provided.

As described above, according to the actuator device of the present embodiment, the space is integrated with the element transmitting electromagnetic interaction and fluid pressure to the output shaft, and thus, the device enables force control with compact size and high output while being back-drivable.

By the integrated structure of the movable element and the piston (elements) and the movable range and the chamber (space), higher output can be ensured as compared with a high-efficiency electromagnetic actuator of the same volume.

(Other Examples of Driving Methods)

Figure 15:
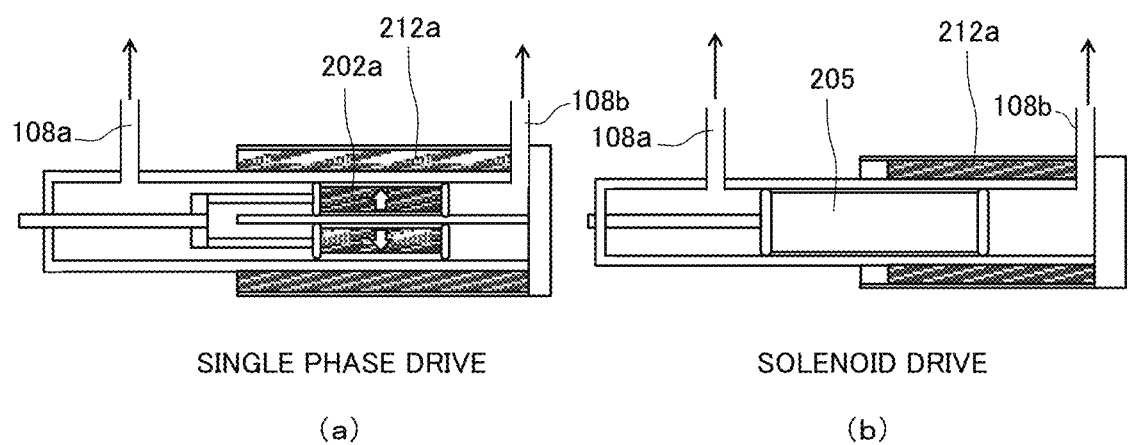
FIG. 15 is a cross-sectional view showing a modification of the method of driving electromagnetic actuator.

FIG. 15 is a cross-sectional view showing a modification of the method of driving electromagnetic actuator.

As shown in FIG. 15(a), as the electromagnetic coil member 110, only a coil 212a is provided, and as the movable element 200, a magnetic member (permanent magnet) 202a generating a magnetic field in the direction perpendicular to the axial direction of cylinder is provided. It is driven by exiting coil 212a with a single phase AC.

Alternatively, as shown in FIG. 15(b), as the magnetic member, a soft magnetic body 205 may be provided in place of permanent magnet 202a.

In this case, the electromagnetic actuator functions as a solenoid actuator and generates driving force. By way of example, when at least a part of magnetic body 205 is outside the coil 212a, a drawing force to the inside of coil member can be generated by exiting coil 212a. Here, coil 212a is housed in a case of soft magnetic body.

In the structure shown in FIG. 15 also, when the movable element is to be driven to the target direction, fluid supply is controlled such that the movable element is driven in the same direction as the direction of relative movement of the movable element caused by the excitation of coil member.

Figure 16:
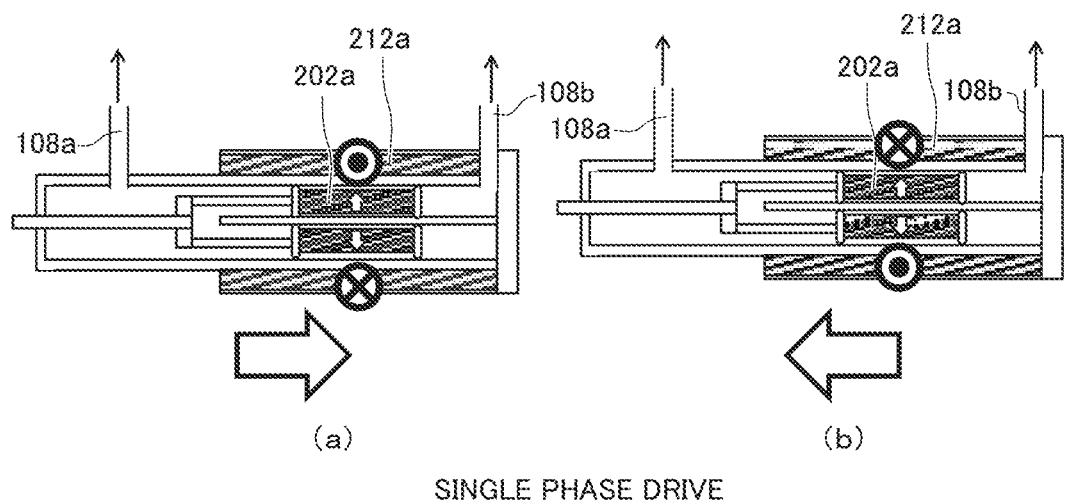
FIG. 16 schematically illustrates coil current in single-phase driving.

FIG. 16 illustrates coil current in single-phase driving, in the structure of FIG. 15(a).

As shown in FIG. 16(a), when a current is caused to flow through coil 212a and the movable element is driven in single phase, the movable element is driven to the right direction, and when the current direction is reversed as shown in FIG. 16(b), the movable element is driven to the left direction.

Figure 17:
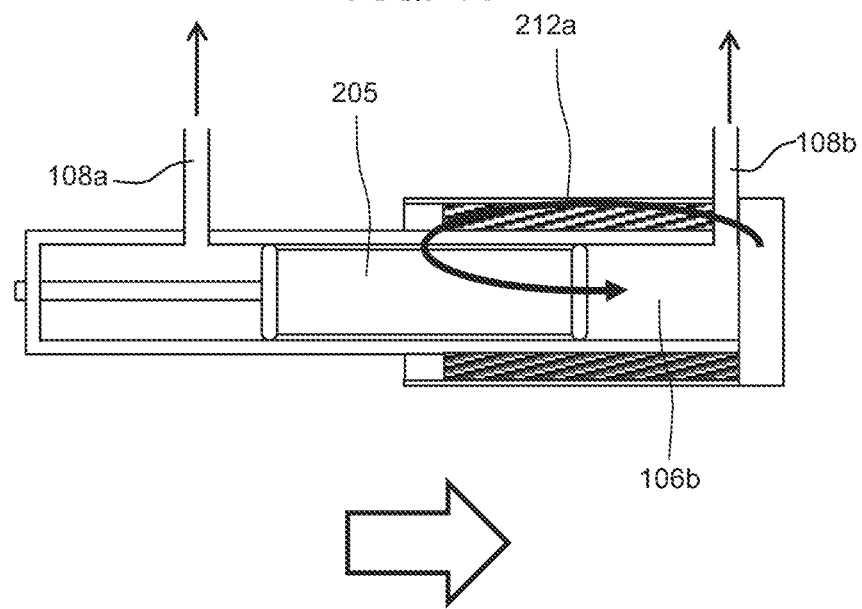
FIG. 17 is a schematic illustration showing a magnetic field generated by the coil.

FIG. 17 is a schematic illustration showing a magnetic field generated by the coil, in the structure of FIG. 15(b).

When the coil is excited with a current, a magnetic flux flows as indicated by an arrow in the figure. At this time, the chamber 106b portion is filled with air and hence, it has low magnetic permeability and high magnetic resistance. The movable element is driven to the right direction to reduce the magnetic resistance of this portion.

The descriptions above have been directed basically to a structure in which a coil is provided on an outer circumference of a cylinder and a permanent magnet is used as the movable element. The present invention, however, is not necessarily limited to such a structure. For example, i) a structure in which the movable element is an electromagnetic coil and the stator arranged on the side of cylinder includes a plurality of permanent magnets generating magnetic fields of prescribed different directions is also possible; and ii) the cylinder is not limited to have a single cylindrical shape but it may have an inner cylinder provided in an outer cylinder with. In this case, a plurality of permanent magnets generating magnetic fields in prescribed different directions are successively arranged inside the inner cylinder and on the outer circumference of the outer cylinder; the movable element is an electromagnetic coil having a cylindrical shape and movable in the space between the inner and outer cylinders, and it may also function as a piston.

Therefore, the term "magnetic element" in its broadest meaning may encompass an electromagnetic coil.

In this structure, as the coil is sandwiched between powerful magnets on the inner and outer sides, a large magnetic flux is generated in the coil. Further, every coil can constantly contribute to the output. Further, as compared with a model using an iron core both in the movable element and the stator, in which thrust pulsation (detent force) generates even without current excitation, in the present model, generation of the detent force can advantageously be avoided.

According to the present embodiment, the actuator device combines force control by electromagnetic force and viscosity/compliance characteristics of working fluid while maintaining back-drivability of both electromagnetic/pneumatic direct drive actuators, whereby a linear driven actuator that can softly respond to external force can be realized.

Further, the actuator device in accordance with the present embodiment is also applicable to a driving mechanism of general industrial products, in addition to the "assist of musculoskeletal movement of a human as an object" described above.

Further, the structure for "assist of musculoskeletal movement of a human as an object" may be used as a robot on its own and, by way of example, it can be used as a humanoid robot.

Embodiment 2

In the above-described structure of pneumatic-electric hybrid actuator device 1000 shown in FIG. 1, air of a prescribed pressure is supplied to/discharged from chamber 106a through duct 108a having a control valve, and air of a prescribed pressure is supplied to/discharged from chamber 106b through duct 108b having a control valve.

The structure of a pneumatic-electric hybrid actuator device 1100 in accordance with Embodiment 2 described in the following differs from the structure of pneumatic-electric hybrid actuator device 1000 or 1000' in accordance with Embodiment 1 in that it has the structure of supplying fluid pressure, for example, air pressure, to chambers 106a and 106b.

As will be described in the following, in Embodiment 2 also, air will be an example of the fluid.

Figure 18:
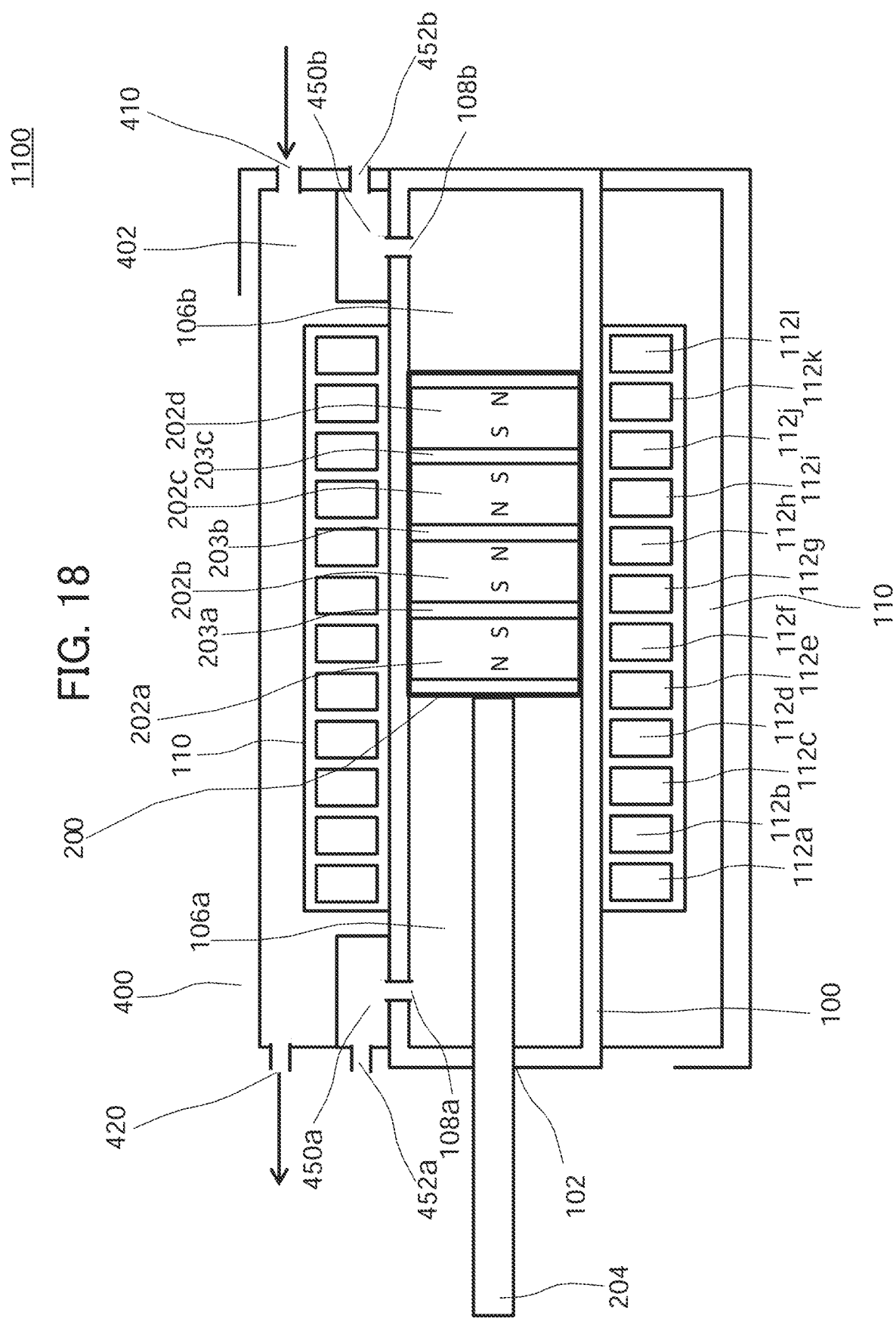
FIG. 18 is an illustration showing a cross-sectional structure of a pneumatic-electric hybrid actuator device 1100 in accordance with Embodiment 2.

FIG. 18 is an illustration showing a cross-sectional structure of a pneumatic-electric hybrid actuator device 1100 in accordance with Embodiment 2. FIG. 18 is to be contrasted with FIG. 1.

In the following, mainly the differences over FIG. 1 will be described. The same components will be denoted by the same reference characters and description thereof will not be repeated.

Referring to FIG. 18, pneumatic-electric hybrid actuator device 1100 is provided with an outer barrel portion 400 covering cylinder 100 and electromagnetic coil member 110. A space defined by outer surfaces of cylinder 100 and electromagnetic coil member 110 and an inner surface of outer barrel portion 400 is fluid-tight and has a function of transmitting air of a prescribed air pressure from the outside. In this sense, this enclosed space will be referred to as a "fluid transmitting path 402."

Air of a prescribed pressure is supplied from an inlet 410 to fluid transmitting path 402. This air is discharged from an outlet 420 of fluid transmitting path 402, and the air of the prescribed pressure discharged from outlet 420 is supplied to an inlet of another actuator device 1100' having the structure similar to pneumatic-electric hybrid actuator device 1100, as will be described later.

Control valves 450a and 450b are provided corresponding to ducts 108a and 108b, respectively.

Control valve 450a supplies the air of the prescribed pressure from fluid transmitting path 402 to chamber 106a, or discharges air from chamber 106a through an outlet 452a, under control of a control unit, not shown.

Similarly, control valve 450b supplies the air of the prescribed pressure from fluid transmitting path 402 to chamber 106b, or discharges air from chamber 106b through an outlet 452b, under control of a control unit, not shown.

When the movable element is to be driven to the target direction, the control unit controls air supply/discharge such that a driving force for driving movable element 200 in the same direction as the relative movement of movable element 200 is caused by excitation of the plurality of coils 112a to 112l.

Figure 19:
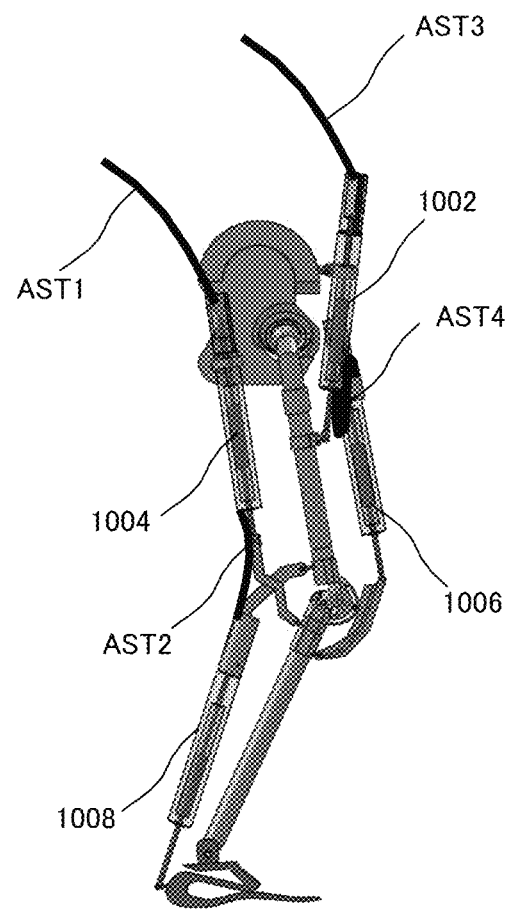
FIG. 19 illustrates air supplying paths when a plurality of actuator devices of the same type are arranged on a skeleton.

FIG. 19 illustrates an air supplying path when a plurality of actuator devices of the same type as pneumatic-electric hybrid actuator device 1100 are arranged on a skeleton.

FIG. 19 is to be contrasted with FIG. 13 and, as in FIG. 13, it shows an example of arrangements of artificial muscles (actuator devices) on an exoskeleton robot for lower limbs.

As shown in FIG. 19, as an artificial muscle for driving inflection of hip joint and extension of knee joint, an actuator device 1004 having a function corresponding to human "hamstring muscle+rectus femoris muscle" is provided on the skeleton, and as an artificial muscle for driving inflection of knee joint, an actuator device 1008 having a function corresponding to human "gastrocnemius muscle" is provided on the skeleton.

As an artificial muscle for driving inflection of hip joint, an actuator device 1002 having a function corresponding to human "iliac muscle+gluteus maximus muscle" is provided on the skeleton, and as an artificial muscle for driving inflection of knee joint and extension of knee joint, an actuator device 1006 having a function corresponding to human "short head of biceps femoris muscle+lateral vastus muscle" is provided on the skeleton.

To inlet 410 of actuator device 1004, compressed air is supplied from a compressed air source (for example, a tank) through a tube AST1, and to inlet 410 (FIG. 18) of actuator device 1008, compressed air is supplied from outlet 420 (FIG. 18) through a tube AST2. By way of example, outlet 420 of actuator device 1008 is sealed.

In the same way, to inlet 410 of actuator device 1002, compressed air is supplied from a compressed air source (for example, a tank) through a tube AST3, and to inlet 410 of actuator device 1006, compressed air is supplied from outlet 420 through a tube AST4. By way of example, outlet 420 of actuator device 1006 is sealed.

Alternatively, though not limiting, the air pressure from outlet 420 of actuator device 1004 may be supplied to inlet 410 of actuator device 1002, and from the compressed air source, compressed air may be supplied to one lower limb of exoskeleton robot through tube AST1 only.

By the structure described above, when air pressure is to be supplied to a plurality of actuator devices, the air pressure supplying path from the compressed air source can be made simpler than in the structure in which air pressure is supplied individually to the plurality of actuator devices.

Further, since the air from the compressed air source is supplied to the outside of electromagnetic coil member 110 in this structure, the effect of air-cooling electromagnetic coil member 110 can also be attained.

Embodiment 3

Figure 20:
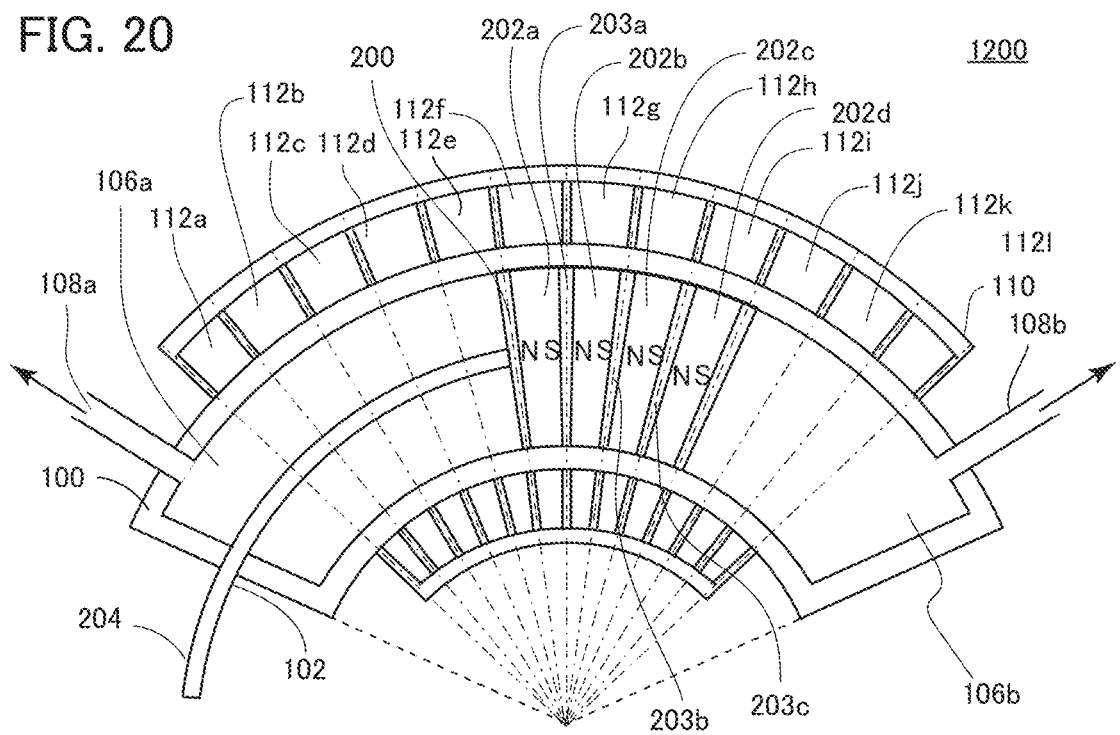
FIG. 20 is an illustration showing a cross-sectional structure of a pneumatic-electric hybrid actuator device 1200 in accordance with Embodiment 3.

FIG. 20 is an illustration showing a cross-sectional structure of a pneumatic-electric hybrid actuator device 1200 in accordance with Embodiment 3. FIG. 20 is to be compared with FIG. 1.

In Embodiment 3 also, air will be an example of the fluid.

In Embodiment 1, cylinder 100 is described as having a straight cylindrical shape.

It is noted, however, that the cylinder shape is not limited to such one and the cylinder shaft may be curved as an arch as shown in FIG. 20.

The structure is the same as that of Embodiment 1 except that the cylinder has the curved shape and, therefore, the same components are denoted by the same reference characters and description thereof will not be repeated.

Embodiment 4

Figure 21:
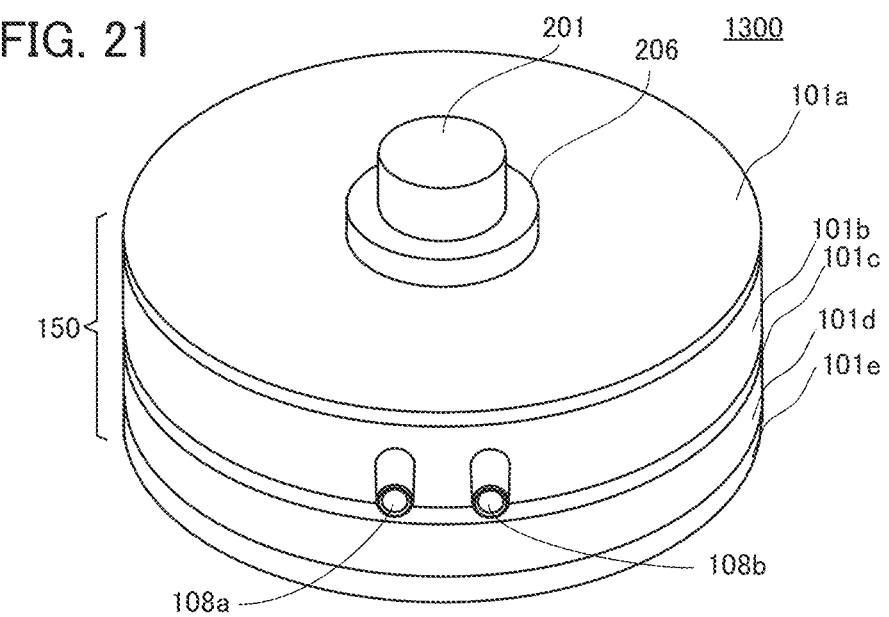
FIG. 21 shows an appearance of a pneumatic-electric hybrid actuator device 1300 in accordance with Embodiment 4.

FIG. 21 shows an appearance of a pneumatic-electric hybrid actuator device 1300 in accordance with Embodiment 4.

Pneumatic-electric hybrid actuator device 1300 drives rotational motion.

Referring to FIG. 21, actuator device 1300 has a stacked structure of cylindrical cases 101*b* and 101*d* having the same radii. At the center of cases 101*b* and 101*d*, an output shaft (rotor) 201 is arranged for transmitting rotary driving force of the movable element in case 101*b* to the outside.

In lower case 101*d*, electromagnetic coils having wires wound around a plurality of sector-shaped cores respectively are arranged to surround the output shaft, as will be described later.

Lower case 101*d* has its bottom portion closed by a back yoke member 101*e* formed of a magnetic material and has a disk shape. Further, an upper opening of lower case 101*d* and a lower opening of upper case 101*b* are separated by a disk-shaped diaphragm 101*c*. An upper opening of upper case 101*b* is closed by an upper lid 101*a*. At the center of upper lid 101*a*, a circular opening is provided though which output shaft 201 passes, with the space between output shaft 201 and the opening being sealed by a bearing 206, so that output shaft 201 can rotate. As will be described later, in order to enable application of an air pressure in case 101*b* with the air of a prescribed pressure through ducts 108*a* and 108*b*, case 101*b*, diaphragm 101*c* and upper lid 101*a* are tight-sealed.

Upper lid 101*a*, case 101*b*, diaphragm 101*c*, case 101*d* and back yoke member 101*e* are collectively referred to as a stator 150 in contrast with the movable element.

FIG. 22 includes schematic illustrations showing inside of stator 150.

Figure 23:
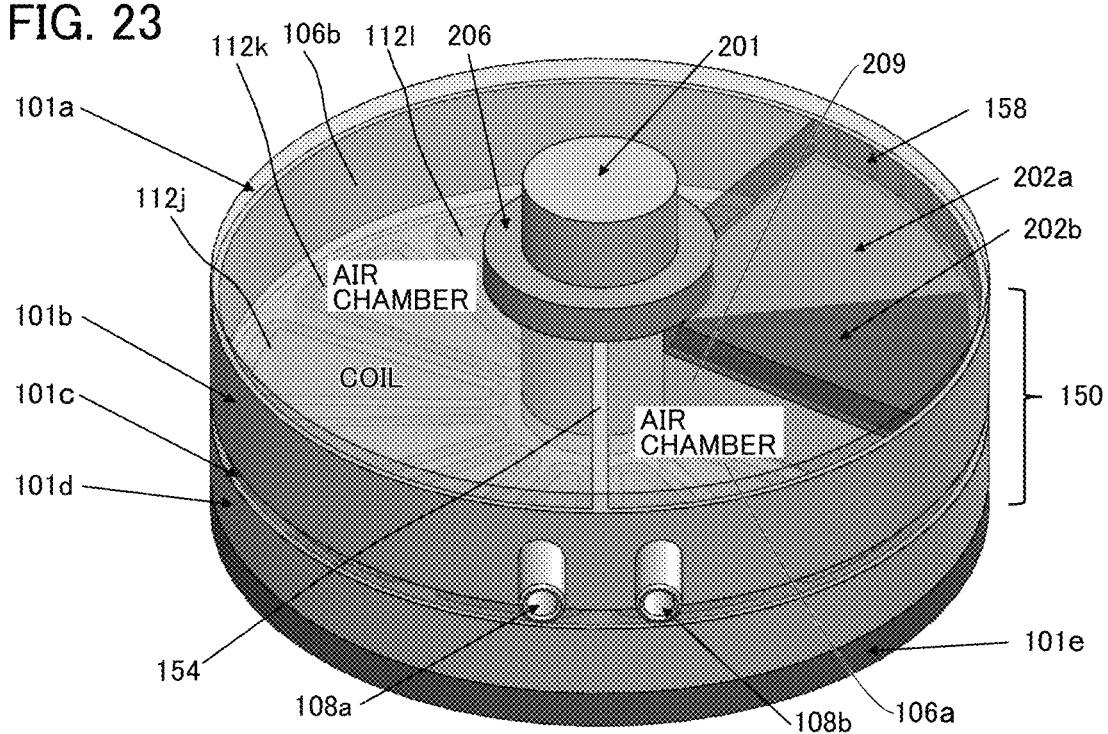
FIG. 23 is a perspective view showing a structure of pneumatic-electric hybrid actuator device 1300.

Further, FIG. 23 is a perspective view showing a structure of pneumatic-electric hybrid actuator device 1300.

In the illustration of FIG. 23, for higher visibility of the inner structure of actuator device 1300, upper lid 101*a* is assumed to be transparent and diaphragm 101*c* is assumed to be semi-transparent.

FIG. 22 (*a*) shows back yoke member 101*e* viewed from above. At the center of back yoke member 101*e*, a bearing 152 is provided for rotatably supporting output shaft 201.

FIG. 22 (*b*) shows the inside of case 101*d* viewed from above.

As shown in FIGS. 22 (*b*) and 23, in case 101*d*, electromagnetic coils 112*a* to 112*l* having wires wound around sector-shaped cores respectively are arranged to surround output shaft 201, as described above.

Though not limiting, electromagnetic coils 112*a* to 112*l* are excited by a three-phase AC applied thereto and drive the movable element.

FIG. 22 (*c*) shows the inside of case 101*b* viewed from above.

As shown in FIGS. 22 (*c*) and 23, in case 101*b*, a movable element 209 (hereinafter referred to as a "rotor 209" as it makes rotational motion) having a sector-shape when viewed from above is provided, and this rotor 209 is configured to move integrally with output shaft 201. By way of example, in rotor 209, two sector-shaped permanent magnets 202*a* and 202*b* are provided next to each other. Permanent magnets 202*a* and 202*b* may be formed by magnetizing a single magnetic element area by area to have such magnetic field directions as will be described below. Permanent magnets 202*a* and 202*b* are magnetized in directions opposite to each other and parallel to output shaft 201. In FIG. 22 (*c*), it is assumed that the permanent magnetic 202*a* and 202*b* are arranged such that the upper surface side of permanent magnet 202*a* is N and the upper surface side of permanent magnet 202*b* is S. The number of permanent magnets may be more than two provided that adjacent ones are magnetized in directions opposite to each other. Though not shown in FIG. 22 (*c*), a magnetic member 158 is provided on permanent magnets 202*a* and 202*b* to cover these, as shown in FIG. 23.

Further, a diaphragm 154 is provided in case 101*b* and a space surrounded by one end surface of rotor 209 and one surface of diaphragm 154 functions as a first chamber 106*a* (also referred to as air chamber), and a space surrounded by the other end surface of rotor 209 and the other surface of diaphragm 154 functions as a second chamber 106*b* (also referred to as air chamber).

FIG. 22 (*d*) shows upper lid 101*a* viewed from above. At the center of upper lid 101*a*, circular opening 156 is provided, through which output shaft 201 passes.

Figure 24:
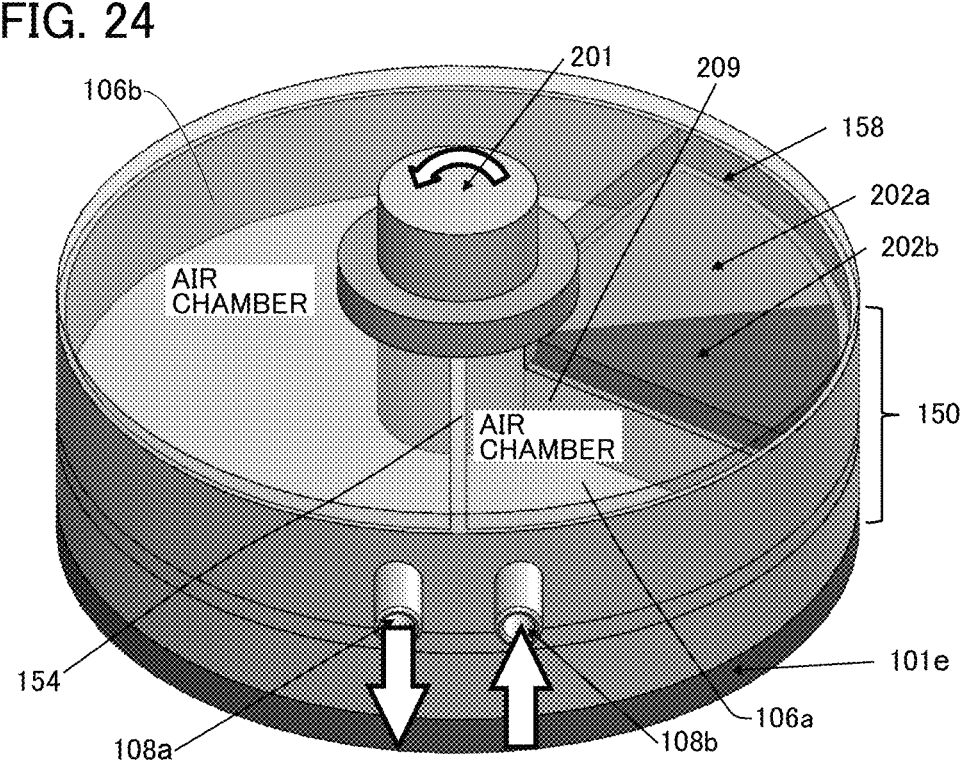
FIG. 24 is a schematic illustration showing an operation of pneumatic-electric hybrid actuator device 1300.

FIG. 24 is an illustration showing an operation of pneumatic-electric hybrid actuator device 1300.

In the illustration of FIG. 24 also, for the sake of visibility of the inner structure of actuator device 1300, upper lid 101a is assumed to be transparent.

Figure 25:
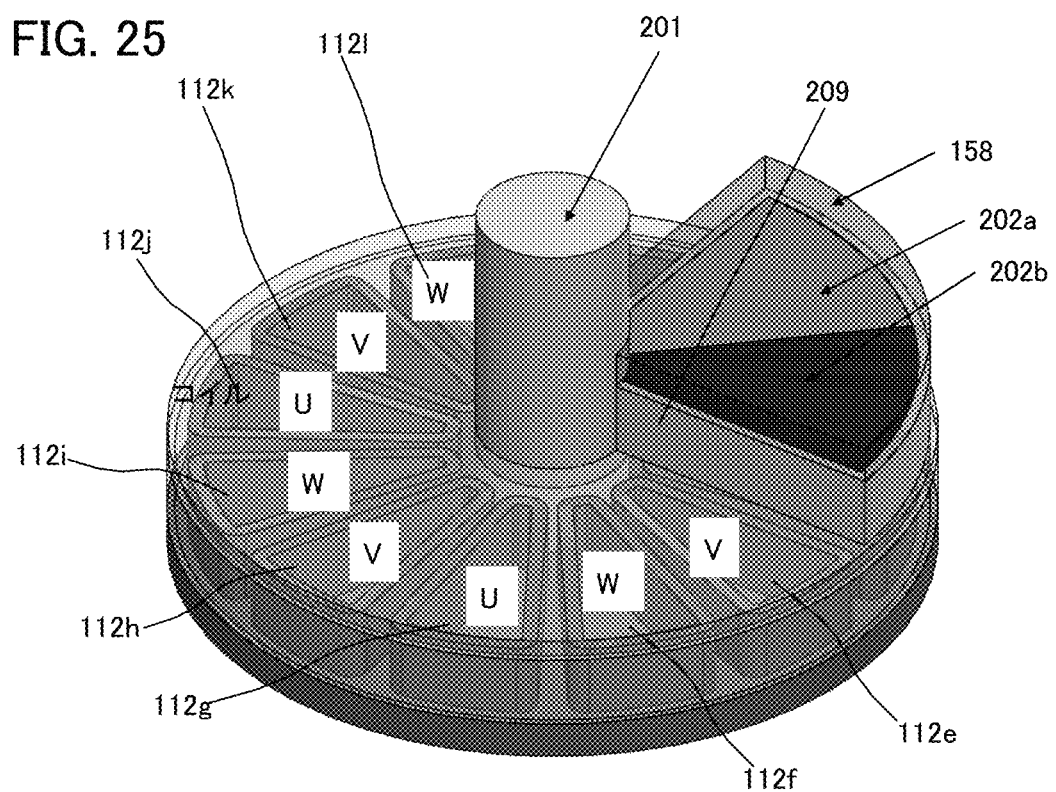
FIG. 25 illustrates a relation of arrangement between electromagnetic coils 112a to 112l and a rotor 209.

FIG. 25 illustrates a relation between arrangements of electromagnetic coils 112a to 112l and rotor 209.

In FIG. 25, for the sake of visibility of positional relation between rotor 209 and the electromagnetic coils, upper lid 101a and case 101b are tentatively removed, and diaphragm 101c and case 101d are assumed to be semi-transparent.

First, referring to FIG. 25, the plurality of coils 112a to 112l are excited in independent polarity directions by independently applied currents. More specifically, the plurality of coils 112a to 112l are configured such that alternative currents of mutually different phases are caused to flow therethrough. By way of example, the plurality of coils may be divided to three sets, with every third one of the plurality of coils 112a to 112l forming each set, and alternate currents having phase shifted by $(2\pi/3)$ from each other (symmetrical three phase AC, with respective phases denoted by U, V and W) are caused to flow to respective sets, whereby rotary thrust is applied to rotor 209.

On the other hand, referring to FIG. 24, the first chamber 106a is a space between one surface of diaphragm 154 and one end surface of rotor 209. The second chamber 106b is a space between the other surface of diaphragm 154 and the other end surface of rotor 209. Air of a prescribed pressure is supplied to or discharged from chamber 106a through a duct 108a with a control valve. Air of a prescribed pressure is supplied to or discharged from chamber 106b through a duct 108b with a control valve.

The rotary drive by the electromagnetic force and air supply/discharge to and from chambers 106a and 106b as described above are controlled by a control unit, not shown. When rotor 209 is to be driven to the target direction, the control unit controls air supply/discharge such that a driving force for driving rotor 209 in the same direction as the relative movement of rotor 209 is caused by excitation of the plurality of coils 112a to 112l.

It is noted that as the fluid, not only a gas such as compressed air but also water, oil or magnetic fluid may be used for the application of an actuator. When compressed air is used, coils can be cooled. When water or oil is used, coil cooling efficiency can be improved, and when magnetic fluid is used, viscosity control becomes possible as a hardware characteristic.

Figure 26:
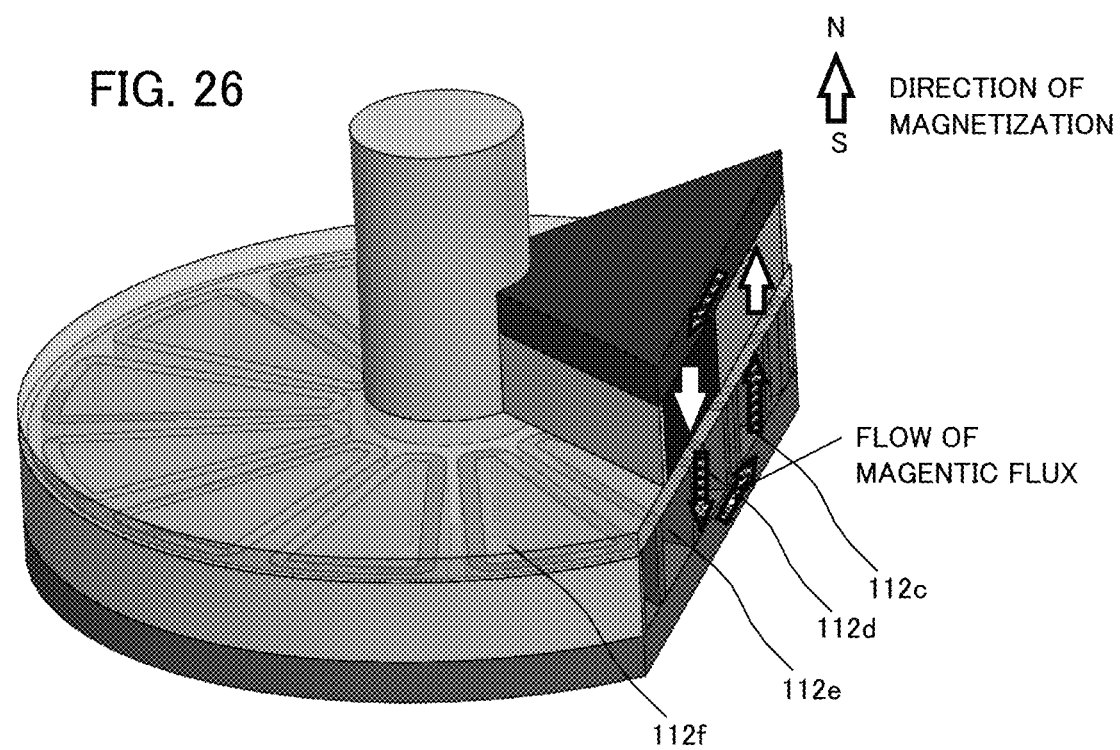
FIG. 26 illustrates a flow of magnetic flux in electromagnetic coils 112a to 112l and in rotor 209.

FIG. 26 illustrates a flow of magnetic flux in electromagnetic coils 112a to 112l and in rotor 209.

FIG. 26 shows a cross-sectional structure of FIG. 25 with parts of the magnetic coils and the rotor tentatively truncated.

When electromagnetic coils 112a to 112l are excited and rotor 209 rotates, at a certain time point, for example, such a flow of magnetic flux as follows occurs: a magnetic flux generated by electromagnetic coil 112c and a magnetic flux of permanent magnet 202a in rotor 209 come to be in the same direction, and the magnetic flux coming out from permanent magnet 202a passes through magnetic member 158, enters an upper surface of permanent magnet 202b, a magnetic flux of permanent magnet 202b and a magnetic flux generated by electromagnetic coil 112d come to be in the same direction, the magnetic flux coming out from electromagnetic coil 112d passes through back yoke member 101e and enters electromagnetic coil 112c.

By the structure as described above, in actuator device 1300 also, as in Embodiment 1, the mechanism for generating electromagnetic driving force and the mechanism for generating air pressure driving force are integrated, and thereby reduction in size is realized and, since not only air pressure but also electromagnetic driving force is utilized, high output with good time responsiveness can be realized.

Modification 1 of Embodiment 4

A structure having permanent magnets facing the side of rotor 209 and electromagnetic coils in case 101d has been described with reference to FIGS. 21 to 26.

It is also possible to provide electromagnetic coils on the side of rotor 209 and to provide permanent magnets on the upper and lower sides thereof.

Figure 27:
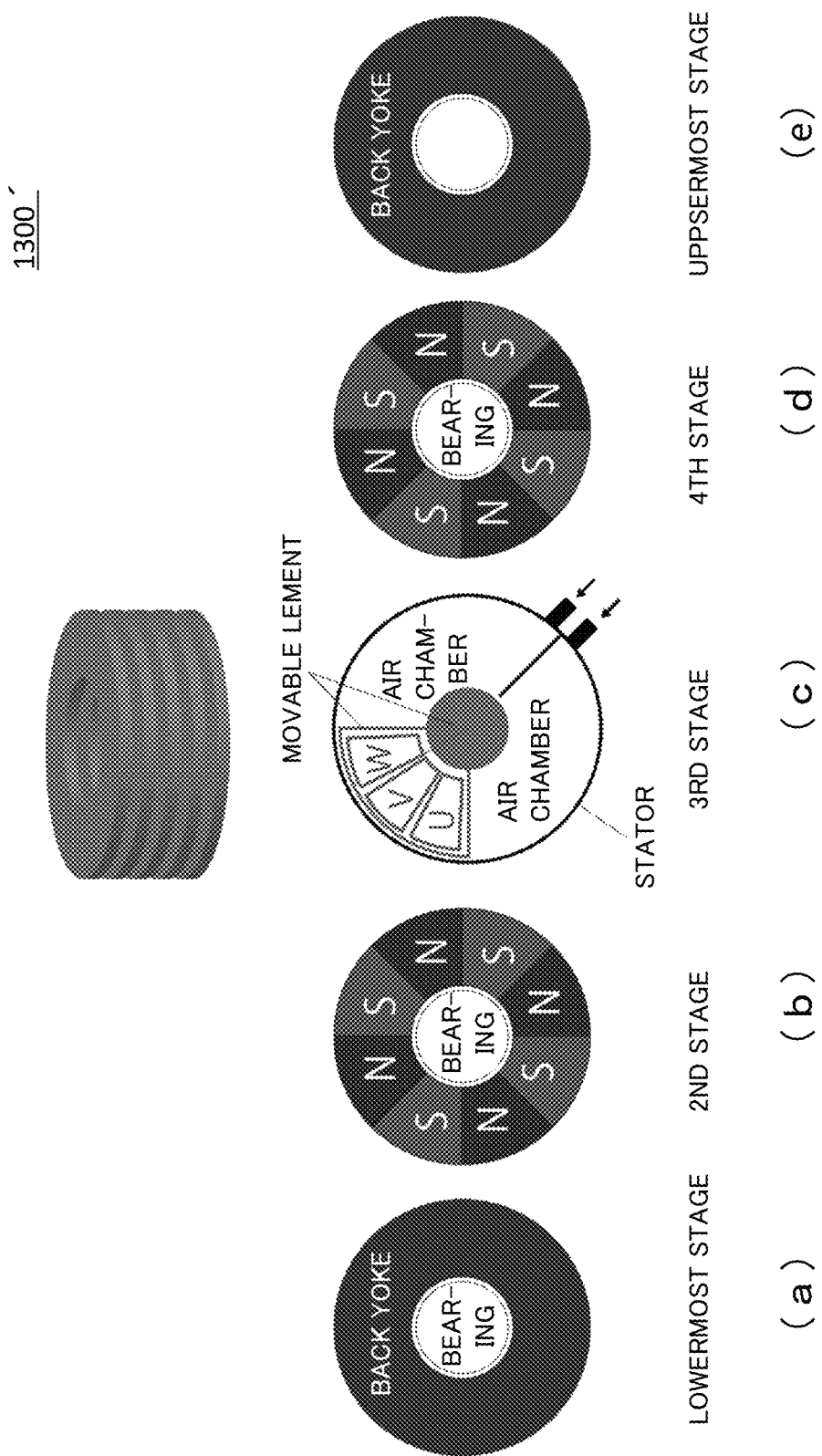
FIG. 27 is a schematic illustration showing a structure of a pneumatic-electric hybrid actuator device 1300' in accordance with Modification 1 of Embodiment 4.

FIG. 27 is an illustration showing such a structure of a pneumatic-electric hybrid actuator device 1300' in accordance with Modification 1 of Embodiment 4.

Figure 28:
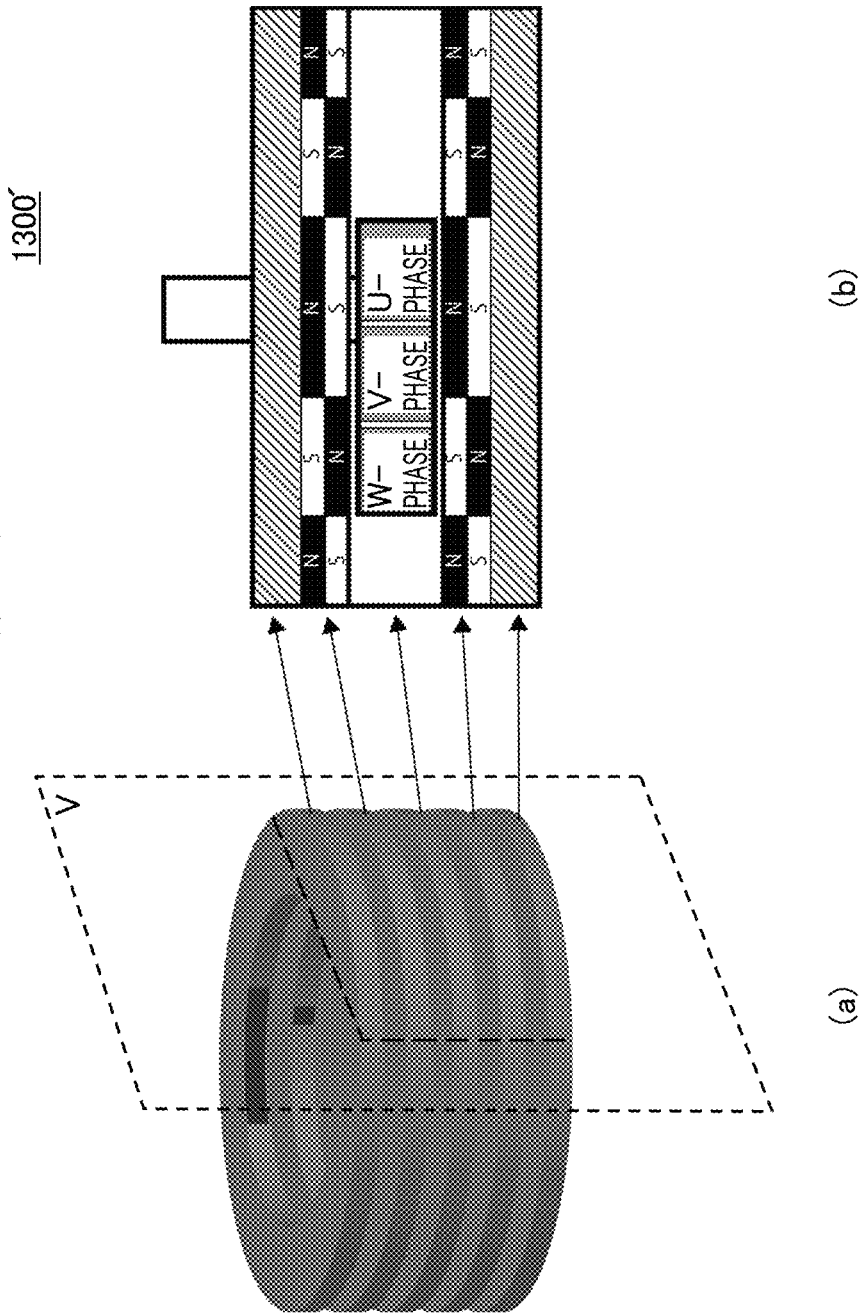
FIG. 28 is an illustration showing a structure of a section perpendicular to the axis of rotation of pneumatic-electric hybrid actuator device 1300' in accordance with Modification 1 of Embodiment 4.

FIG. 28 is an illustration showing a structure of a section perpendicular to the axis of rotation of pneumatic-electric hybrid actuator device 1300' in accordance with Modification 1 of Embodiment 4. FIG. 28 (b) shows a cross-section of an imaginary plane V of FIG. 28 (a).

Referring to FIG. 27 (a), as in Embodiment 4, a back yoke is provided at the lowermost stage.

Next, as shown in FIG. 27 (b), in a first case on the back yoke, a plurality of sector-shaped permanent magnets are arranged around output shaft 201 such that the magnetic flux is in the direction to the output shaft and that direction of magnetization is alternately reversed between adjacent permanent magnets. FIG. 27 (b) shows, as an example, a structure having eight permanent magnets arranged alternately.

As shown in FIG. 27 (c), in a second case upper than the first case, as in case 101b of FIG. 23, a movable element (rotor) is provided in a rotatable manner. In the rotor, electromagnetic coils formed by winding wires around three sector-shaped core members respectively are provided, allowing individual application of UVW alternate currents. It is noted, however, that the number of electromagnetic coils is not limited to three, and a larger number of coils may be used.

The second case is tightly sealed as is case 101b of FIG. 23, and it is configured to independently apply air pressure of a prescribed pressure to the first and second air chambers.

As shown in FIG. 27 (d), in a third case upon the second case, a plurality of sector-shaped permanent magnets are arranged around output shaft 201 such that the magnetic fluxes are in the directions to the output shaft and that the directions of magnetization are alternately reversed between adjacent permanent magnets. In FIG. 27 (d), eight permanent magnets are arranged alternately, in accordance with the structure shown in FIG. 27 (b). As to the magnetizing direction of each permanent magnet shown in FIG. 27 (d), the direction of magnetization is the same as the permanent magnet at the corresponding position in the first case, as shown in FIG. 28.

As shown in FIG. 27 (e), at the uppermost stage, a back yoke member is provided as an upper lid. At the center of back yoke member as the upper lid, an opening is formed, through which output shaft 201 passes.

Such a structure also attains the same effects as attained by pneumatic-electric hybrid actuator device 1300 of Embodiment 4.

Modification 2 of Embodiment 4

In pneumatic-electric hybrid actuator device 1300 of Embodiment 4, electromagnetic coils 112a to 112l (generally referred to as electromagnetic coil 112) generating a driving force for the permanent magnets in rotor 209 are provided in case 101d below case 101b containing rotor 209.

Figure 29:
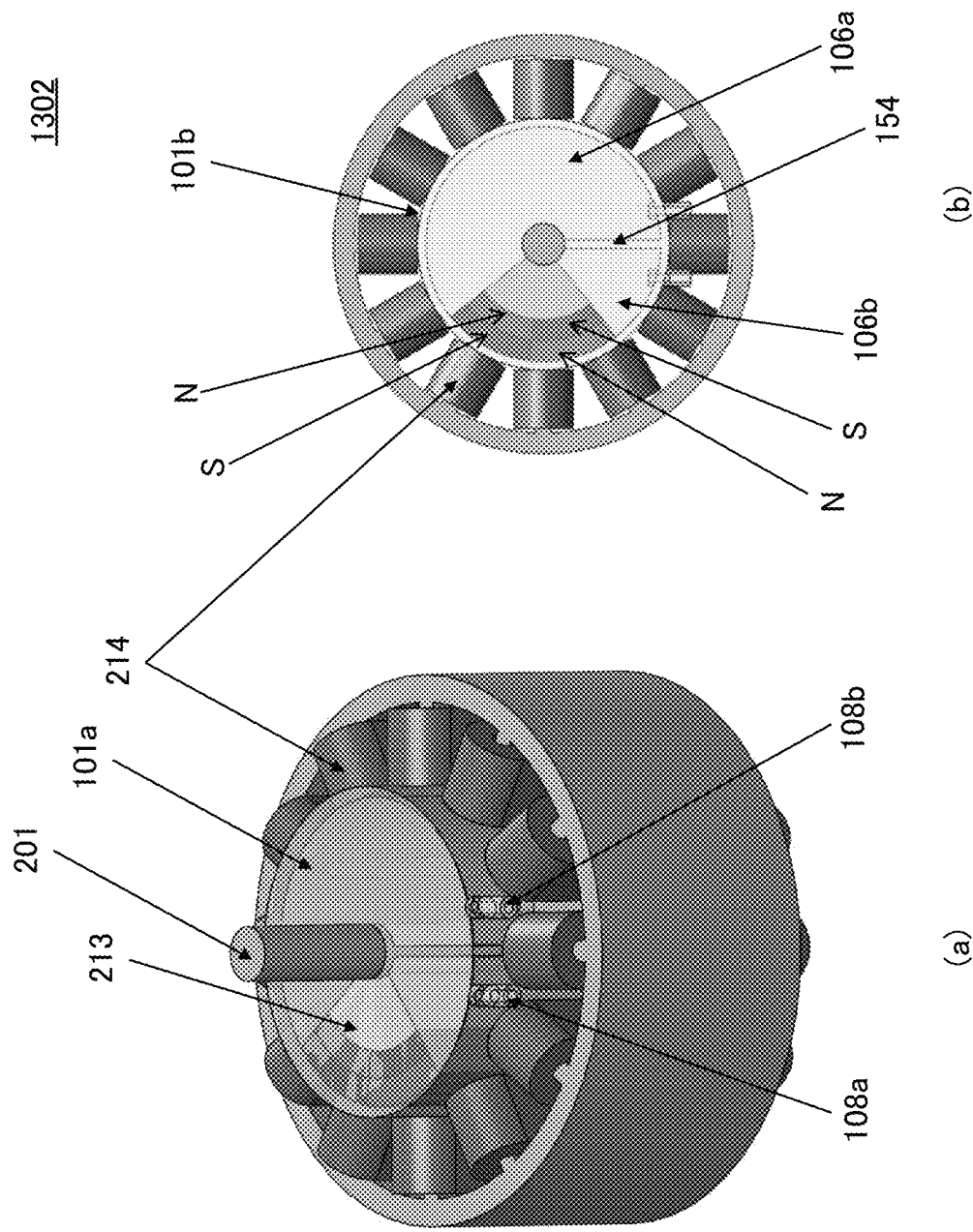
FIG. 29 is an illustration showing a structure of a pneumatic-electric hybrid actuator device 1302 in accordance with Modification 2 of Embodiment 4.

FIG. 29 is an illustration showing a structure of a pneumatic-electric hybrid actuator device 1302 in accordance with Modification 2 of Embodiment 4.

FIG. 29 (*a*) is a perspective view with upper lid 101*a* drawn as semi-transparent. FIG. 29 (*b*) shows the structure of FIG. 29 (*a*) viewed from above.

Electromagnetic coils 214 are arranged along an outer circumference of case 101b containing a rotor 213. Accordingly, the permanent magnets in rotor 213 are magnetized in the direction perpendicular to the rotation axis (radial direction of rotor).

The pneumatic-electric hybrid actuator device 1300 of Embodiment 4 or pneumatic-electric hybrid actuator device 1300' or 1302 as the modification of Embodiment 4, when controlled in the similar manner as in Embodiment 1, realizes rotary drive actuator capable of softly responding to external force, by the combination of force control by electromagnetic force and viscosity/compliance characteristic of working fluid, while maintaining back-drivability of both electromagnetic/pneumatic direct drive actuators.

The pneumatic-electric hybrid actuator device 1300 of Embodiment 4 or pneumatic-electric hybrid actuator device 1300' or 1302 as the modification of Embodiment 4 can be used as an actuator device for the rotational motion of joint portions of exoskeleton robots such as shown in FIGS. 13 and 14, and it can be used for "assist of musculoskeletal movement of a human as an object" and can also be applied to a driving mechanism of general industrial products.

The configuration of such "assist of musculoskeletal movement of a human as an object" can also be used as a single robot, and it can be applied, for example, to a humanoid robot.

Embodiment 5

In Embodiment 4, rotors 209 and 213 move in an arc. In Embodiment 5, a structure in which the rotor moves continuously will be described.

Figure 30:
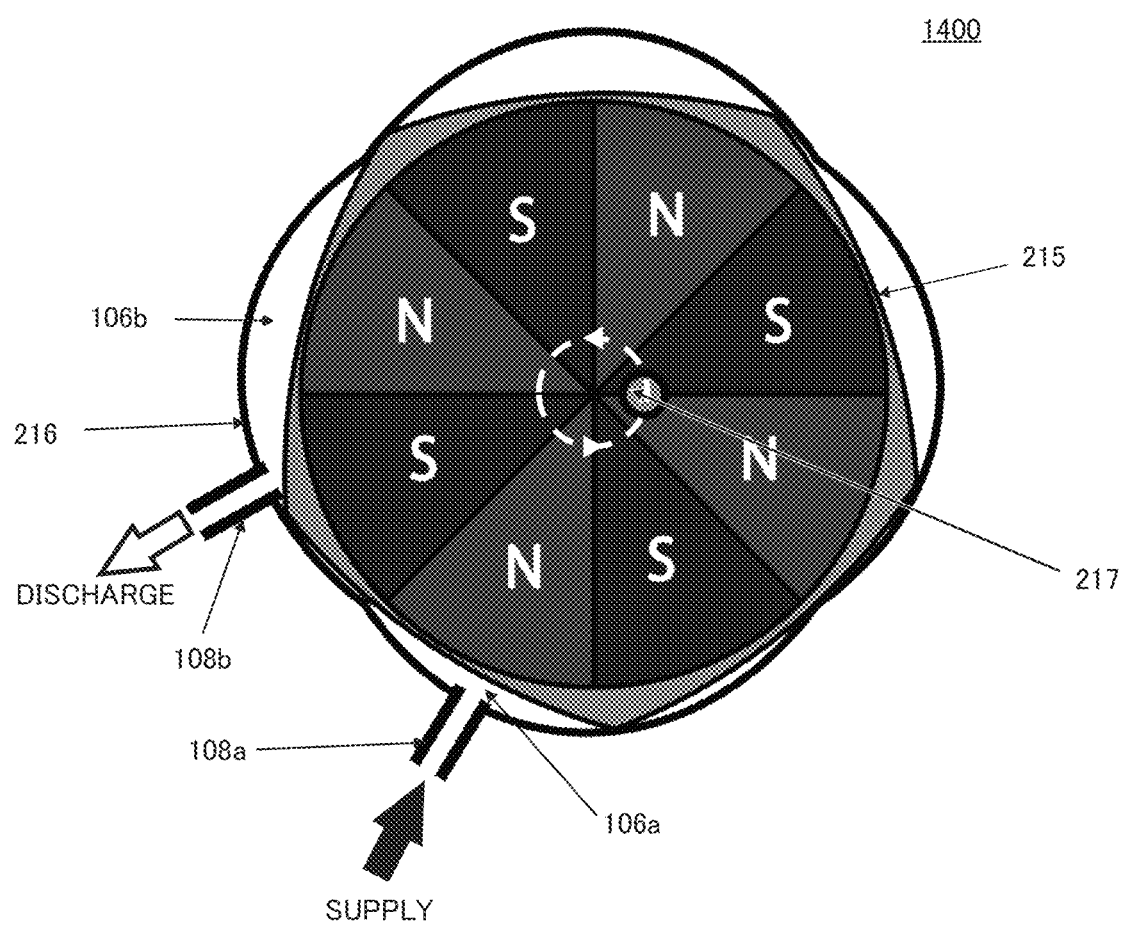
FIG. 30 is an illustration showing a structure of a pneumatic-electric hybrid actuator device 1400 in accordance with Embodiment 5.

FIG. 30 is an illustration showing a structure of a pneumatic-electric hybrid actuator device 1400 in accordance with Embodiment 5.

A figure that always has a constant width is referred to as a "curve of constant width." A circle is a typical curve of constant width. Another well-known example of the curve of constant width is a Reuleaux polygon.

Specifically, a rotary engine of which rotor has a Reuleaux triangle has been known. Here, the rotor is formed by three lobes of inner envelopes inscribed in a trochoid curve of a rotor housing containing the rotor. At the center of the rotor, there is a circular hole to which an eccentric shaft is attached with a rotor bearing interposed, and an internal gear with internal teeth to be engaged with the gear of a side housing is provided on its circumference. The rotor housing has a cocoon shape, of which inner side surface has a 2-node peritrochoid curve.

More generally, a rotor having a cross-sectional shape of the curve of constant width is known to be able to rotate smoothly, constantly in contact with an inner surface of the housing, with the housing having an inner envelope shape fitting the cross-sectional shape of the rotor.

FIG. 30 shows, as an example, a rotor 215 having a cross-sectional shape of the curve of constant width based on a pentagon, a housing 216 having as its inner cross-sectional shape a peritrochoid curve along a rotational trajectory of rotor 215, and an output shaft 217 for transmitting to the outside the driving force by rotor 215.

In rotor 215, there are a plurality of permanent magnets, arranged such that adjacent magnets have direction of magnetization made opposite to each other.

The output shaft 217 is eccentric and, therefore, an opening allowing eccentric rotation of the output shaft is formed in upper lid 101*a*, and this opening is tight-sealed at the upper surface side of rotor 215. The driving force of rotation of rotor 215 can be transmitted to the outside by a crank mechanism.

As a result, output shaft 217 come to rotate in the same direction as the rotation of rotor 215.

Alternatively, as in the case of the rotary engine described above, a structure in which the driving force is transmitted to the outside by an eccentric shaft is also possible.

In accordance with the rotation of rotor 215, air of a prescribed pressure is supplied (air supply) or discharged through ducts 108*a* and 108*b* at prescribed timing, whereby driving force by electromagnetic force as well as driving force by air pressure can be generated.

By way of example, in FIG. 30, an inner surface corresponding to the first lobe of the cross section of housing 216 and an outer side surface of rotor 215 are in contact at a first contact portion. Further, an inner surface corresponding to the second lobe adjacent to the first lobe of the cross-section of housing 216 and an outer side surface of rotor 215 are in contact with each other at a second contact portion. In this manner, by the outer side surface of rotor 215 from the first to second contact portion and the corresponding inner surfaces of housing 216 form air chambers 106*a* and 106*b*. Volumes of such air chambers change as rotor 215 rotates. Air is supplied to/discharged from air chambers 106*a* and 106*b* through ducts 108*a* and 108*b* at prescribed timing in a controlled manner.

By way of example, at the time point shown in FIG. 30, at the timing of discharging air (indicated by a white arrow in the figure) from air chamber 106*b* to duct 108*b*, an operation of supplying air to air chamber 106*a* through duct 108*a* takes place (as indicated by a black arrow in the figure). By controlling the timing of supplying and discharging air, it becomes possible to generate driving force by air pressure in addition to the driving force by electromagnetic force as described above.

Here, the duct for supplying and discharging air may be provided corresponding to another lobe of the cross-section of housing 216 and the number of ducts is not limited to two in departure from FIG. 30.

It is noted that in the structure of FIG. 30, electromagnetic coils are provided at a stage lower than the housing 216 containing rotor 215 as in FIG. 22.

It is noted, however, that as in Modification 2 of Embodiment 4 described above, the electromagnetic coils may be arranged along the outer circumference of housing 216 containing rotor 215. In that case, the direction of magnetization of permanent magnets in rotor 215 is perpendicular to the rotation axis as in Modification 2 of Embodiment 4.

As described above, by the structure of Embodiment 5, it becomes possible to have the pneumatic-electric hybrid actuator device rotate continuously and to take out the driving force to the outside.

The embodiments as have been described here are mere examples and should not be interpreted as restrictive. The scope of the present invention is determined by each of the claims with appropriate consideration of the written description of the embodiments and embraces modifications within the meaning of, and equivalent to, the languages in the claims.

INDUSTRIAL APPLICABILITY

The present invention is applicable to an actuator device for driving various mechanical parts as well as to a power assist device supporting movement of a user using the same.

REFERENCE SIGNS LIST 1 exoskeleton robot, 100 cylinder, 101a upper lid, 101b case, 101c diaphragm, 101d case, 101e back yoke member, 102 opening, 106a, 106b chamber, 108a, 108b air supplying/discharging duct, 110 electromagnetic coil member, 112a-112l coil, 200 movable element, 202a-202d magnetic member, 201, 204, 217 output shaft, 206 bearing, 209, 215 rotor, 216 housing, 1000, 1100, 1200, 1300 actuator device.

The invention claimed is:

1. An actuator device, comprising:
a fluid-tight housing configured to allow application of a fluid pressure of a prescribed fluid from outside to inside;
a movable element contained in said fluid-tight housing and slidable in accordance with said fluid pressure in said fluid-tight housing;
a driving member for transmitting a driving force of said movable element to the outside of said fluid-tight housing; and
a first magnetic member provided outside of said fluid-tight housing along a moving path of said movable element; wherein
said first magnetic member includes an electromagnetic coil member;
said movable element has a second magnetic member and is moved relative to said first magnetic member by excitation of said first or second magnetic member;
said fluid-tight housing has a first chamber defined as a space between a first inner surface of said fluid-tight housing and one side surface of said movable element, and a second chamber defined as a space between a second inner surface of said fluid-tight housing and another side surface opposite to said one side surface of said movable element;
said actuator device further comprising:
fluid pressure supplying conduits having respective control valves for supplying said fluid pressure to each of said first and second chambers, wherein
said first magnetic member extends over portions of both the first and second chambers where, inside the fluid-tight housing, the fluid pressure for driving the movable element is supplied; and
said control valves control supply of said fluid pressure such that said movable element is driven in the same direction as a direction of relative movement of said movable element caused by excitation of said first or second magnetic member wherein
said fluid-tight housing is a cylinder capable of keeping fluid-tight state;
said driving member is an output shaft transmitting rotational motion of said movable element to the outside of said cylinder;
said movable element is a rotor rotating integrally with said output shaft in said cylinder, wherein
said cylinder includes a diaphragm having one surface and another surface opposite to said one surface, and extending from said output shaft to an inner circumference of said cylinder provided in said cylinder; and
said first and second inner surfaces are the one surface and another surface of said diaphragm.

2. The actuator device according to claim 1, wherein
said first magnetic member is an electromagnetic coil member provided on a bottom surface side of said cylinder; and
said electromagnetic coil member is excited for relative movement of said rotor.

3. The actuator device according to claim 2, wherein
said electromagnetic coil member has a plurality of coils to be excited independently, provided in a circumferential direction on the bottom surface side of said cylinder;
said second magnetic member includes a plurality of sector-shaped permanent magnets arranged adjacent to each other in said rotor; and
said permanent magnets are arranged such that adjacent ones have opposite polarities alternately in the direction of said output shaft.

4. The actuator device according to claim 1, wherein
said first magnetic member has a plurality of coils to be independently excited, provided along an outer circumference of said cylinder;
said second magnetic member includes a plurality of sector-shaped permanent magnets arranged adjacent to each other in said rotor; and
said permanent magnets are arranged to have opposite polarities alternately in the normal direction of said output shaft.

5. A humanoid robot of which skeleton is driven by the actuator device according to claim 1.

* * * * *